(12) United States Patent
Chang et al.

(10) Patent No.: US 9,713,700 B2
(45) Date of Patent: Jul. 25, 2017

(54) APPARATUS AND METHODS FOR DILATING AND MODIFYING OSTIA OF PARANASAL SINUSES AND OTHER INTRANASAL OR PARANASAL STRUCTURES

(71) Applicant: Acclarent, Inc., Menlo Park, CA (US)

(72) Inventors: John Y. Chang, Los Altos, CA (US); Joshua Makower, Los Altos, CA (US); Julia D. Vrany, Los Altos, CA (US); Amrish Jayprakash Walke, Milpitas, CA (US)

(73) Assignee: Acclarent, Inc., Irvine, CA (US)

( * ) Notice: Subject to any disclaimer, the term of this patent is extended or adjusted under 35 U.S.C. 154(b) by 102 days.

(21) Appl. No.: 14/566,845

(22) Filed: Dec. 11, 2014

(65) Prior Publication Data
US 2015/0182735 A1 Jul. 2, 2015

Related U.S. Application Data

(63) Continuation of application No. 12/768,963, filed on Apr. 28, 2010, now Pat. No. 8,945,088, which is a
(Continued)

(51) Int. Cl.
*A61B 17/00* (2006.01)
*A61M 29/02* (2006.01)
(Continued)

(52) U.S. Cl.
CPC ........... *A61M 29/02* (2013.01); *A61B 5/6852* (2013.01); *A61B 17/24* (2013.01);
(Continued)

(58) Field of Classification Search
CPC .......... A61B 17/32002; A61B 17/3421; A61B 2017/22051; A61B 2018/00327;
(Continued)

(56) References Cited

U.S. PATENT DOCUMENTS 3,447,061 A 5/1969 Russell et al.
5,378,234 A 1/1995 Hammerslag et al.
(Continued)

FOREIGN PATENT DOCUMENTS

JP S61-16750 1/1986
JP H01-305965 12/1989
(Continued)

OTHER PUBLICATIONS

Japanese OA, Notification of Reasons for Refusal dated Mar. 22, 2016 for JP 2012-266049 U.S. Appl. No. 15/187,938, filed Jun. 21, 2016.

*Primary Examiner* — Kevin C Sirmons
*Assistant Examiner* — Deanna K Hall
(74) *Attorney, Agent, or Firm* — Frost Brown Todd LLC

(57) ABSTRACT

Sinusitis and other disorders of the ear, nose and throat are diagnosed and/or treated using minimally invasive approaches with flexible or rigid instruments. Various methods and devices are used for remodeling or changing the shape, size or configuration of a sinus ostium or duct or other anatomical structure in the ear, nose or throat; implanting a device, cells or tissues; removing matter from the ear, nose or throat; delivering diagnostic or therapeutic substances or performing other diagnostic or therapeutic procedures. Introducing devices (e.g., guide catheters, tubes, guidewires, elongate probes, other elongate members) may be used to facilitate insertion of working devices (e.g. catheters e.g. balloon catheters, guidewires, tissue cutting or remodeling devices, devices for implanting elements like stents, electrosurgical devices, energy emitting devices, devices for delivering diagnostic or therapeutic agents, substance delivery implants, scopes etc.) into the paranasal sinuses or other structures in the ear, nose or throat.

20 Claims, 35 Drawing Sheets

Related U.S. Application Data continuation of application No. 11/928,346, filed on Oct. 30, 2007, now Pat. No. 8,172,828, which is a continuation of application No. 10/944,270, filed on Sep. 17, 2004, now abandoned, which is a continuation-in-part of application No. 10/829,917, filed on Apr. 21, 2004, now Pat. No. 7,654,997.

(51) Int. Cl.

| | | |
|---|---|---|
| *A61B 17/24* | (2006.01) | |
| *A61B 17/34* | (2006.01) | |
| *A61F 2/18* | (2006.01) | |
| *A61F 2/958* | (2013.01) | |
| *A61M 25/10* | (2013.01) | |
| *A61B 5/00* | (2006.01) | |
| *A61B 18/14* | (2006.01) | |
| *A61F 2/82* | (2013.01) | |
| *A61F 2/95* | (2013.01) | |
| *A61M 25/00* | (2006.01) | |
| *A61M 25/01* | (2006.01) | |
| *A61M 25/09* | (2006.01) | |
| *A61B 17/32* | (2006.01) | |
| *A61B 17/22* | (2006.01) | |
| *A61F 2/90* | (2013.01) | |
| *A61B 18/00* | (2006.01) | |
| *A61B 34/20* | (2016.01) | |

(52) U.S. Cl.
CPC ...... *A61B 17/3403* (2013.01); *A61B 18/1492* (2013.01); *A61F 2/186* (2013.01); *A61F 2/82* (2013.01); *A61F 2/95* (2013.01); *A61F 2/958* (2013.01); *A61M 25/005* (2013.01); *A61M 25/0026* (2013.01); *A61M 25/0082* (2013.01); *A61M 25/0102* (2013.01); *A61M 25/0138* (2013.01); *A61M 25/0147* (2013.01); *A61M 25/09* (2013.01); *A61M 25/10* (2013.01); *A61B 17/32002* (2013.01); *A61B 17/3421* (2013.01); *A61B 2017/22039* (2013.01); *A61B 2017/22051* (2013.01); *A61B 2017/22061* (2013.01); *A61B 2018/00327* (2013.01); *A61B 2018/00595* (2013.01); *A61B 2034/2051* (2016.02); *A61F 2/90* (2013.01); *A61M 25/1006* (2013.01); *A61M 25/1011* (2013.01); *A61M 2025/0177* (2013.01); *A61M 2025/109* (2013.01); *A61M 2025/1072* (2013.01); *A61M 2025/1079* (2013.01); *A61M 2029/025* (2013.01); *A61M 2210/0681* (2013.01); *A61M 2210/1028* (2013.01)

(58) Field of Classification Search
CPC ............ A61F 2/186; A61F 2/82; A61F 2/958; A61M 2025/0177; A61M 2210/0681; A61M 25/005; A61M 25/0082; A61M 25/0102; A61M 25/0138; A61M 25/0147
See application file for complete search history.

(56) References Cited

U.S. PATENT DOCUMENTS

| | | |
|---|---|---|
| 6,645,223 B2 | 11/2003 | Boyle et al. |
| 6,679,871 B2 | 1/2004 | Hahnen |
| 6,855,136 B2 | 2/2005 | Dorros et al. |
| 6,860,849 B2 | 3/2005 | Matsushita et al. |
| 7,037,321 B2 | 5/2006 | Sachdeva et al. |
| 7,634,233 B2 | 12/2009 | Deng et al. |
| 7,727,226 B2 | 6/2010 | Chang et al. |
| 8,002,740 B2 | 8/2011 | Willink et al. |
| 8,100,933 B2 | 1/2012 | Becker |
| 8,190,389 B2 | 5/2012 | Kim et al. |
| 8,439,687 B1 | 5/2013 | Morriss et al. |
| 8,740,292 B2 | 6/2014 | Kishi |
| 8,961,495 B2 | 2/2015 | Chang et al. |
| 9,089,258 B2 | 7/2015 | Goldfarb et al. |
| 2003/0009095 A1* | 1/2003 | Skarda ............... A61B 18/1492 600/374 |
| 2007/0282305 A1 | 12/2007 | Goldfarb et al. |
| 2008/0183128 A1 | 7/2008 | Morriss et al. |
| 2010/0030031 A1 | 2/2010 | Goldfarb et al. |
| 2010/0274188 A1 | 10/2010 | Chang et al. |

FOREIGN PATENT DOCUMENTS

| | | |
|---|---|---|
| JP | H05-506805 | 10/1993 |
| JP | H10-501159 | 2/1998 |

\* cited by examiner

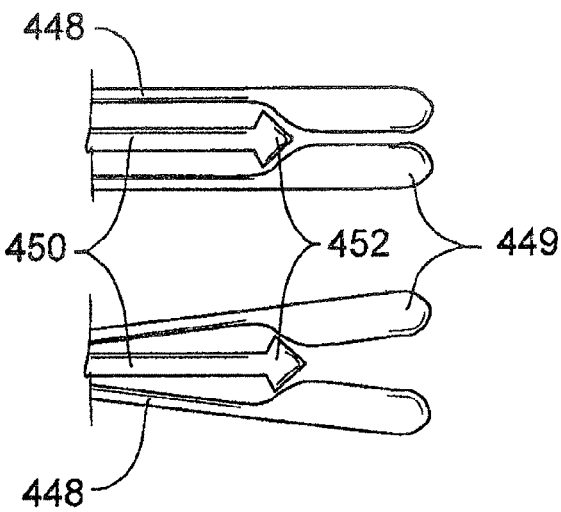
*Fig. 4L*
*Fig. 4M*
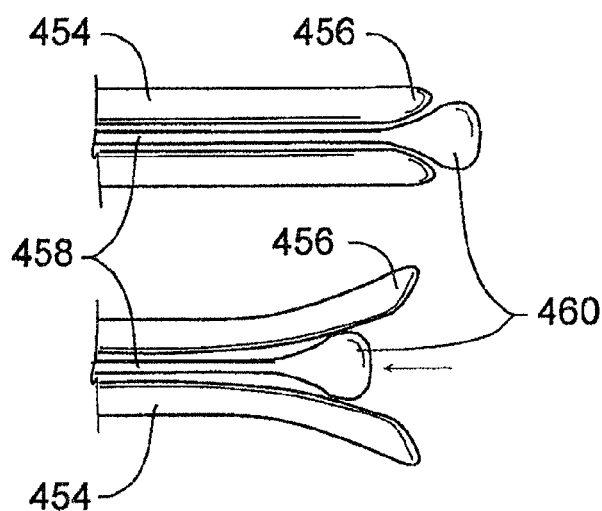
*Fig. 4N*
*Fig. 4O*
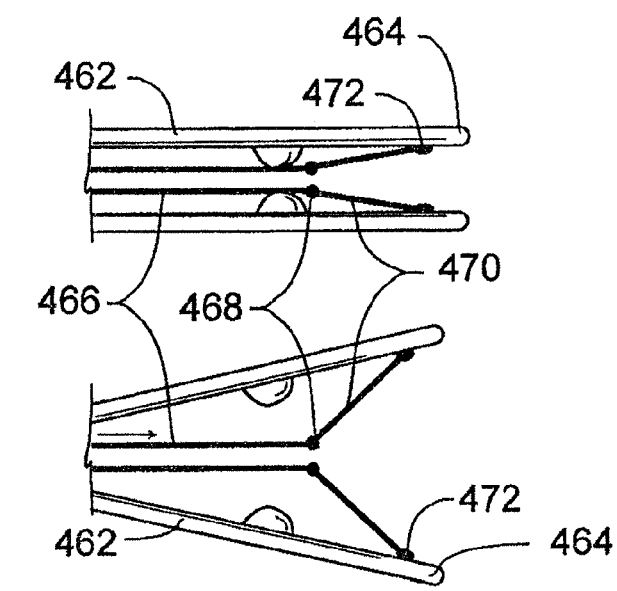
*Fig. 4P*
*Fig. 4Q*

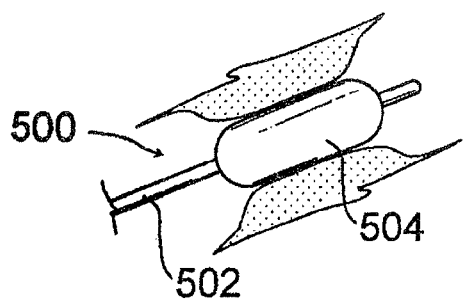 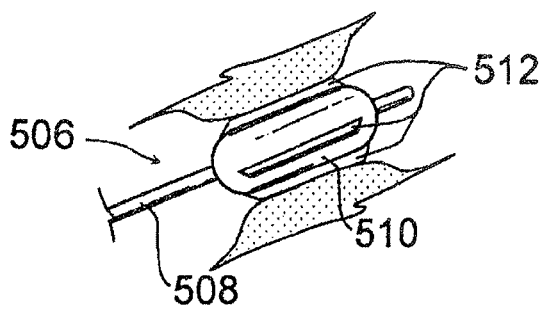
Fig. 5 O    Fig. 5 P
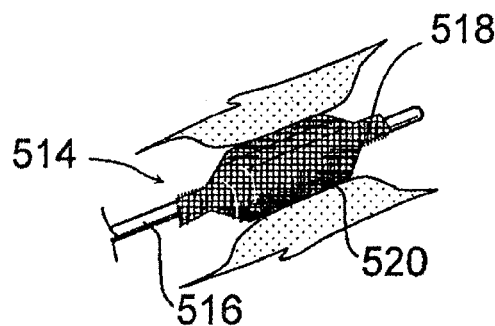
Fig. 5 Q
Fig. 6 F
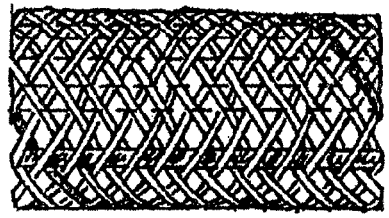
Fig. 6 F '

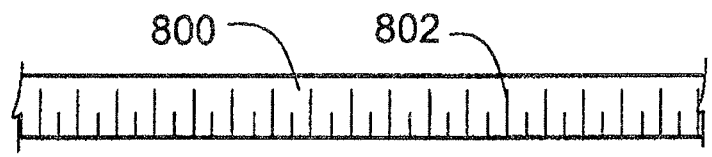
Fig. 8A
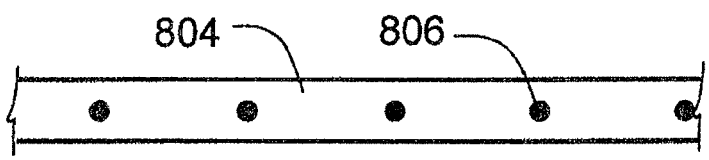
Fig. 8B
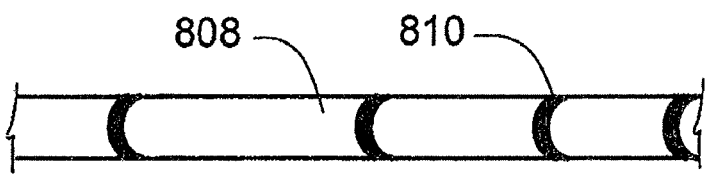
Fig. 8C
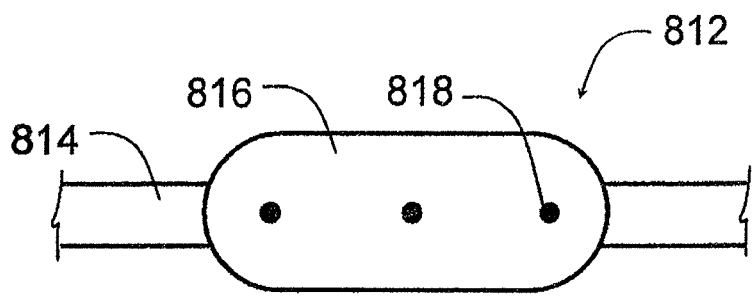
Fig. 8D
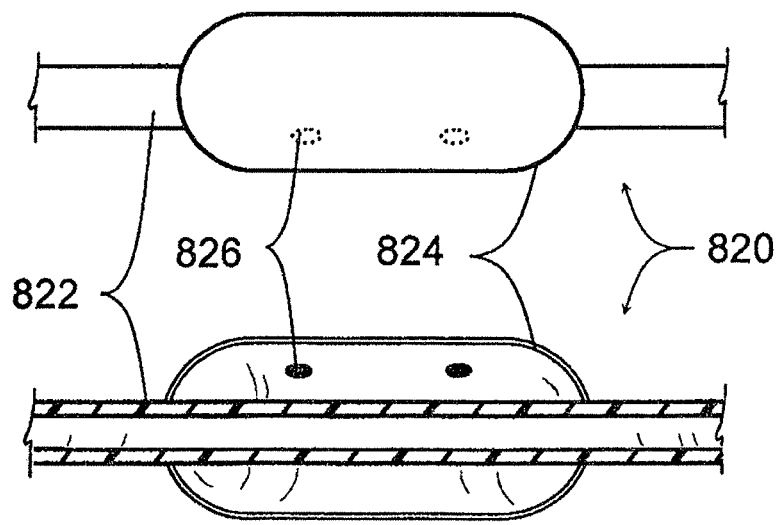
Fig. 8E
Fig. 8E'

APPARATUS AND METHODS FOR DILATING AND MODIFYING OSTIA OF PARANASAL SINUSES AND OTHER INTRANASAL OR PARANASAL STRUCTURES

RELATED APPLICATIONS

This application is a continuation of U.S. patent application Ser. No. 12/768,963, entitled "Apparatus and Methods for Dilating and Modifying Ostia of Paranasal Sinuses and Other Intranasal or Paranasal Structures," filed on Apr. 28, 2010, issued as U.S. Pat. No. 8,945,088, which is a continuation of U.S. patent application Ser. No. 11/928,346, entitled "Apparatus and Methods for Dilating and Modifying Ostia of Paranasal Sinuses and Other Intranasal or Paranasal Structures," filed on Oct. 30, 2007, issued as U.S. Pat. No. 8,172,828, which is a continuation of U.S. patent application Ser. No. 10/944,270, entitled "Apparatus and Methods for Dilating and Modifying Ostia of Paranasal Sinuses and Other Intranasal or Paranasal Structures," filed on Sep. 17, 2004, published as United States Patent Publication No. 2006/0004323, now abandoned, which is a continuation-in-part of U.S. patent application Ser. No. 10/829,917, entitled "Devices, Systems and Methods for Diagnosing and Treating Sinusitis and Other Disorders of the Ears, Nose and/or Throat," filed on Apr. 21, 2004, issued as U.S. Pat. No. 7,654,997, the entire disclosures of which are expressly incorporated herein by reference.

BACKGROUND

The present invention relates generally to medical devices and methods and more particularly to minimally invasive, devices, systems and methods for treating sinusitis and other ear, nose & throat disorders.

The nose is responsible for warming, humidifying and filtering inspired air and for conserving heat and moisture from expired air. The nose is formed mainly of cartilage, bone, mucous membranes and skin.

The bones in the nose contain a series of cavities known as paranasal sinuses that are connected by passageways. The paranasal sinuses include frontal sinuses, ethmoid sinuses, sphenoid sinuses and maxillary sinuses. The paranasal sinuses are lined with mucous-producing epithelial tissue and ultimately opening into the nasal cavity. Normally, mucous produced by the epithelial tissue slowly drains out of each sinus through an opening known as an ostium. If the epithelial tissue of one of these passageways becomes inflamed for any reason, the cavities which drain through that passageway can become blocked. This blockage can be periodic (resulting in episodes of pain) or chronic. This interference with drainage of mucous (e.g., occlusion of a sinus ostium) can result in mucosal congestion within the paranasal sinuses. Chronic mucosal congestion of the sinuses can cause damage to the epithelium that lines the sinus with subsequent decreased oxygen tension and microbial growth (e.g., a sinus infection).

Sinusitis:

The term "sinusitis" refers generally to any inflammation or infection of the paranasal sinuses caused by bacteria, viruses, fungi (molds), allergies or combinations thereof. It has been estimated that chronic sinusitis (e.g., lasting more than 3 months or so) results in 18 million to 22 million physician office visits per year in the United States.

Patients who suffer from sinusitis typically experience at least some of the following symptoms:

headaches or facial pain
nasal congestion or post-nasal drainage
difficulty breathing through one or both nostrils
bad breath
pain in the upper teeth Thus, one of the ways to treat sinusitis is by restoring the lost mucous flow. The initial therapy is drug therapy using anti-inflammatory agents to reduce the inflammation and antibiotics to treat the infection. A large number of patients do not respond to drug therapy. Currently, the gold standard for patients with chronic sinusitis that do not respond to drug therapy is a corrective surgery called Functional Endoscopic Sinus Surgery.

Current and Proposed Procedures for Sinus Treatment

Functional Endoscopic Sinus Surgery

In FESS, an endoscope is inserted into the nose and, under visualization through the endoscope, the surgeon may remove diseased or hypertrophic tissue or bone and may enlarge the ostia of the sinuses to restore normal drainage of the sinuses. FESS procedures are typically performed with the patient under general anesthesia.

Although FESS continues to be the gold standard therapy for surgical treatment of severe sinus disease, FESS does have several shortcomings. For example, FESS can cause significant post-operative pain. Also, some FESS procedures are associated with significant postoperative bleeding and, as a result, nasal packing is frequently placed in the patient's nose for some period of time following the surgery. Such nasal packing can be uncomfortable and can interfere with normal breathing, eating, drinking etc. Also, some patients remain symptomatic even after multiple FESS surgeries. Additionally, some FESS procedures are associated with risks of iatrogenic orbital, intracranial and sinonasal injury. Many otolaryngologists consider FESS an option only for patients who suffer from severe sinus disease (e.g., those showing significant abnormalities under CT scan). Thus, patients with less severe disease may not be considered candidates for FESS and may be left with no option but drug therapy. One of the reasons why FESS procedures can be bloody and painful relates to the fact that instruments having straight, rigid shafts are used. In order to target deep areas of the anatomy with such straight rigid instrumentation, the physician needs to resect and remove or otherwise manipulate any anatomical structures that may lie in the direct path of the instruments, regardless of whether those anatomical structures are part of the pathology.

Balloon Dilation Based Sinus Treatment

Methods and devices for sinus intervention using dilating balloons have been disclosed in U.S. Pat. No. 2,525,183 (Robison) and United States Patent Publication No. 2004/0064150 A1 (Becker), now U.S. Pat. No. 8,317,816, issued Nov. 27, 2012. For example, U.S. Pat. No. 2,525,183 (Robison) discloses an inflatable pressure device which can be inserted following sinus surgery and inflated within the sinus. The patent does not disclose device designs and methods for flexibly navigating through the complex nasal anatomy to access the natural ostia of the sinuses. The discussion of balloon materials is also fairly limited to thin flexible materials like rubber which are most likely to be inadequate for dilating the bony ostia of the sinus.

United States patent publication number 2004/0064150 A1, issued as U.S. Pat. No. 8,317,816 (Becker) discloses balloon catheters formed of a stiff hypotube to be pushed into a sinus. The balloon catheters have a stiff hypotube with a fixed pre-set angle that enables them to be pushed into the sinus. In at least some procedures wherein it is desired to position the balloon catheter in the ostium of a paranasal sinus, it is necessary to advance the balloon catheter through complicated or tortuous anatomy in order to properly position the balloon catheter within the desired sinus ostium. Also, there is a degree of individual variation in the intranasal and paranasal anatomy of human beings, thus making it difficult to design a stiff-shaft balloon catheter that is optimally shaped for use in all individuals. Indeed, rigid catheters formed of hypotubes that have pre-set angles cannot be easily adjusted by the physician to different shapes to account for individual variations in the anatomy. In view of this, the Becker patent application describes the necessity of having available a set of balloon catheters, each having a particular fixed angle so that the physician can select the appropriate catheter for the patient's anatomy. The requirement to test multiple disposable catheters for fit is likely to be very expensive and impractical. Moreover, if such catheter are disposable items (e.g., not sterilizable and reusable) the need to test and discard a number of catheters before finding one that has the ideal bend angle could be rather expensive.

Methods and devices for sinus intervention using dilating balloons have been disclosed in U.S. Pat. No. 2,525,183 (Robison) and United States Patent Publication No. 2004/0064150 A1, issued as U.S. Pat. No. 8,317,816 (Becker). For example, U.S. Pat. No. 2,525,183 (Robison) discloses an inflatable pressure device which can be inserted following sinus surgery and inflated within the sinus. The patent does not disclose device designs and methods for flexibly navigating through the complex nasal anatomy to access the natural ostia of the sinuses. The discussion of balloon materials is also fairly limited to thin flexible materials like rubber which are most likely to be inadequate for dilating the bony ostia of the sinus.

United States patent publication number 2004/0064150 A1, issued as U.S. Pat. No. 8,317,816 (Becker) discloses balloon catheters formed of a stiff hypotube to be pushed into a sinus. The balloon catheters have a stiff hypotube with a fixed pre-set angle that enables them to be pushed into the sinus. In at least some procedures wherein it is desired to position the balloon catheter in the ostium of a paranasal sinus, it is necessary to advance the balloon catheter through complicated or tortuous anatomy in order to properly position the balloon catheter within the desired sinus ostium. Also, there is a degree of individual variation in the intranasal and paranasal anatomy of human beings, thus making it difficult to design a stiff-shaft balloon catheter that is optimally shaped for use in all individuals. Indeed, rigid catheters formed of hypotubes that have pre-set angles cannot be easily adjusted by the physician to different shapes to account for individual variations in the anatomy. In view of this, the Becker patent application describes the necessity of having available a set of balloon catheters, each having a particular fixed angle so that the physician can select the appropriate catheter for the patient's anatomy. The requirement to test multiple disposable catheters for fit is likely to be very expensive and impractical. Moreover, if such catheter are disposable items (e.g., not sterilizable and reusable) the need to test and discard a number of catheters before finding one that has the ideal bend angle could be rather expensive.

SUMMARY

In general, the present invention provides methods, devices and systems for diagnosing and/or treating sinusitis or other conditions of the ear, nose or throat.

In accordance with the present invention, there are provided methods wherein one or more flexible or rigid elongate devices as described herein are inserted in to the nose, nasopharynx, paranasal sinus, middle ear or associated anatomical passageways to perform an interventional or surgical procedure. Examples of procedures that may be performed using these flexible catheters or other flexible elongate devices include but are not limited to: remodeling or changing the shape, size or configuration of a sinus ostium or other anatomical structure that affects drainage from one or more paranasal sinuses; cutting, ablating, debulking, cauterizing, heating, freezing, lasing, forming an osteotomy or trephination in or otherwise modifying bony or cartilaginous tissue within paranasal sinus or elsewhere within the nose; removing puss or aberrant matter from the paranasal sinus or elsewhere within the nose; scraping or otherwise removing cells that line the interior of a paranasal sinus; delivering contrast medium; delivering a therapeutically effective amount of a therapeutic substance; implanting a stent, tissue remodeling device, substance delivery implant or other therapeutic apparatus; cutting, ablating, debulking, cauterizing, heating, freezing, lasing, dilating or otherwise modifying tissue such as nasal polyps, abberant or enlarged tissue, abnormal tissue, etc.; grafting or implanting cells or tissue; reducing, setting, screwing, applying adhesive to, affixing, decompressing or otherwise treating a fracture; delivering a gene or gene therapy preparation; removing all or a portion of a tumor; removing a polyp; delivering histamine, an allergen or another substance that causes secretion of mucous by tissues within a paranasal sinus to permit assessment of drainage from the sinus; implanting a cochlear implant or indwelling hearing aid or amplification device, etc.

Still further in accordance with the invention, there are provided devices and systems for performing some or all of the procedures described herein. Introducing devices may be used to facilitate insertion of working devices (e.g. catheters e.g. balloon catheters, tissue cutting or remodeling devices, guidewires, devices for implanting elements like stents, electrosurgical devices, energy emitting devices, devices for delivering diagnostic or therapeutic agents, substance delivery implants, scopes etc) into the paranasal sinuses and other structures in the ear, nose or throat.

Still further in accordance with the invention, there are provided apparatus and methods for navigation and imaging of the interventional devices within the sinuses using endoscopic including stereo endoscopic, fluoroscopic, ultrasonic, radiofrequency localization, electromagnetic, magnetic and other radiative energy based modalities. These imaging and navigation technologies may also be referenced by computer directly or indirectly to pre-existing or simultaneously created 3-D or 2-D data sets which help the doctor place the devices within the appropriate region of the anatomy.

Further aspects, details and embodiments of the present invention will be understood by those of skill in the art upon reading the following detailed description of the invention and the accompanying drawings.

BRIEF DESCRIPTION OF THE DRAWINGS

FIGS. 2Y through 2AC are partial coronal sectional views through a human head showing various steps of a method for treating a mucocele in a frontal sinus.

FIGS. 4L and 4M show sectional views of a mechanical dilator that comprises a pushable member.

FIGS. 4N and 4O show sectional views of a mechanical dilator that comprises a pullable member.

FIGS. 4P and 4Q show sectional views of a mechanical dilator that comprises a hinged member.

FIGS. 4R through 4W are schematic diagrams of alternative configurations for the distal portions of mechanical dilators of the types shown in FIGS. 4H through 4Q.

FIG. 4S' shows a partial perspective view of the outer stationary member of FIG. 4R.

FIG. 4U' shows a partial perspective view of the outer hemi-tubular member of FIG. 4T.

FIG. 4W' shows a partial perspective view of the outer curved member of FIG. 4V.

FIG. 5O shows a partial perspective view of a balloon catheter device comprising a balloon for delivering diagnostic or therapeutic substances.
FIG. 5P shows a partial perspective view of a balloon/cutter catheter device comprising a balloon with one or more cutter blades.
FIG. 5Q shows a perspective view of a balloon catheter device comprising a balloon with a reinforcing braid attached on the external surface of the balloon.
FIG. 5R shows a partial sectional view of a balloon catheter wherein inflation ports are located near the distal end of the balloon.
FIG. 5S shows a partial sectional view of an embodiment of a balloon catheter comprising multiple balloons inflated by a single lumen.
FIG. 5T shows a partial sectional view of a balloon catheter comprising multiple balloons inflated by multiple lumens.
FIGS. 5U through 5AB show perspective and sectional views of various embodiments of balloon catheters having sensors mounted thereon or therein.

FIG. 6F' is an enlarged side view of the braid of the device of FIG. 6F.

FIG. 8A shows a partial perspective view of a catheter shaft comprising distance markers.

FIG. 8B shows a partial perspective view of a catheter shaft comprising one type of radiopaque markers.

FIG. 8C shows a partial perspective view of a catheter shaft comprising another type of radiopaque markers.

FIG. 8D shows a partial perspective view of a balloon catheter comprising an array of radiopaque markers arranged on the outer surface of the balloon.

FIG. 8E shows a partial perspective view of a balloon catheter comprising an array of radiopaque markers arranged on an inner surface of the balloon.

FIG. 8E' is a longitudinal sectional view of FIG. 8E.

DETAILED DESCRIPTION

The following detailed description, the accompanying drawings and the above-set-forth Brief Description of the Drawings are intended to describe some, but not necessarily all, examples or embodiments of the invention. The contents of this detailed description do not limit the scope of the invention in any way.

A number of the drawings in this patent application show anatomical structures of the ear, nose and throat. In general, these anatomical structures are labeled with the following reference letters:

| | |
|---|---|
| Nasal Cavity | NC |
| Nasopharynx | NP |
| Frontal Sinus | FS |
| Ethmoid Sinus | ES |
| Ethmoid Air Cells | EAC |
| Sphenoid Sinus | SS |
| Sphenoid Sinus Ostium | SSO |
| Maxillary Sinus | MS |
| Mucocele | MC |

Figure 1:
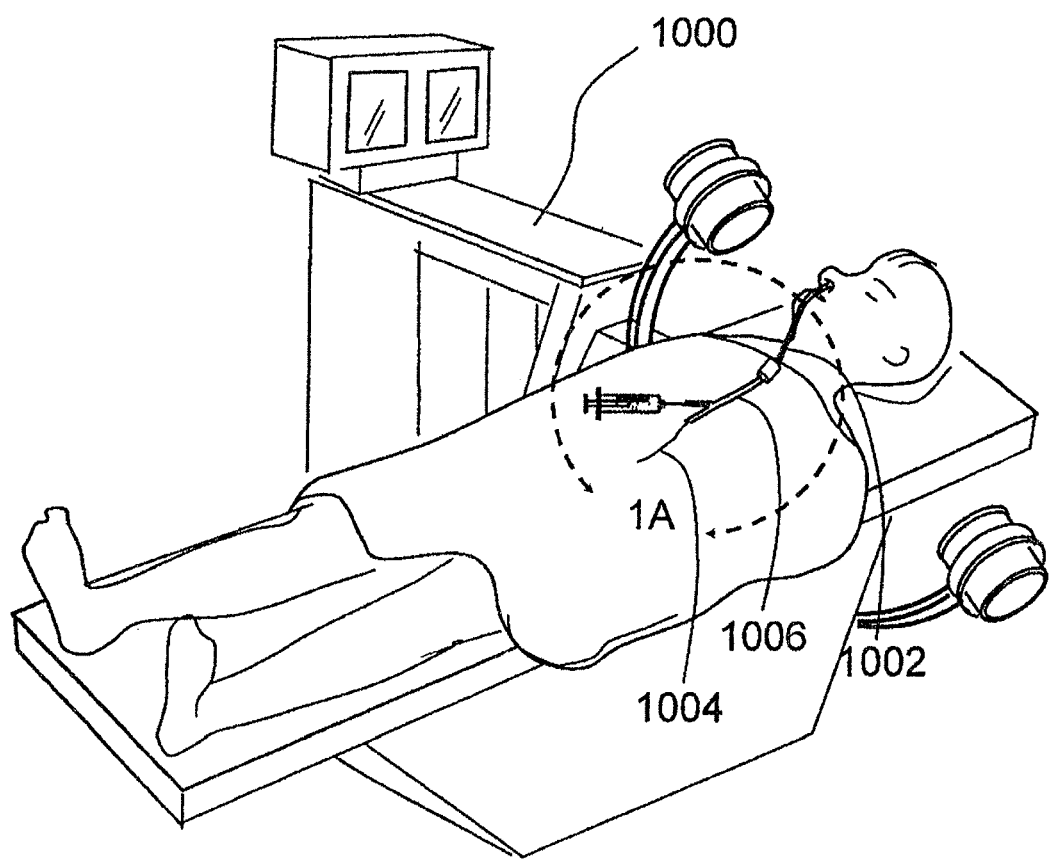
FIG. 1 shows a schematic diagram of a system for catheter-based minimally invasive sinus surgery of the present invention being used to perform a sinus surgery procedure on a human patient.
Figure 1A:
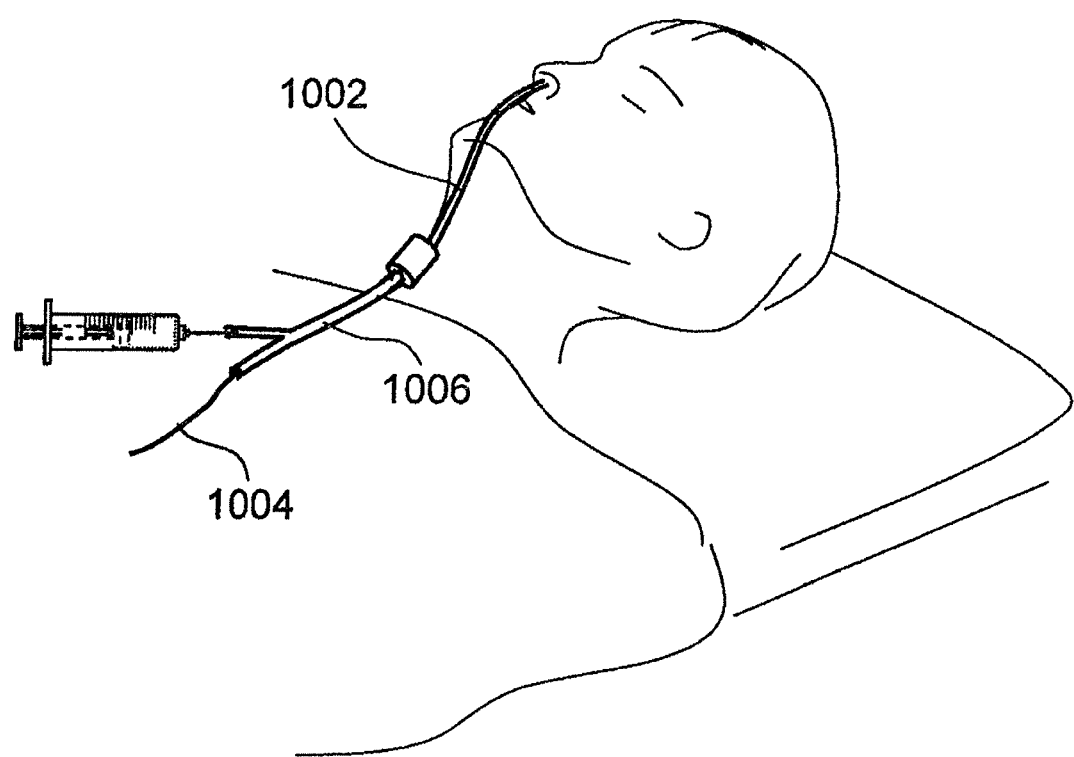
FIG. 1A is an enlarged view of portion "1A" of FIG. 1.

FIGS. 1 and 1A provide a general showing of a minimally invasive surgery system of the present invention comprising a C-arm fluoroscope 1000 that is useable to visualize a first introducing device 1002 (e.g., a guide catheter or guide tube), a second introducing device 1004 (e.g., a guidewire or elongate probe) and a working device 1006 (e.g., a balloon catheter, other dilation catheter, debrider, cutter, etc.). FIGS. 2A-8E' show certain non-limiting examples of the introducing devices 1002 (e.g., a guide catheter or guide tube), 1004 (guides, guidewires, elongate probes, etc.) and working devices 1006 (e.g., a balloon catheters, other dilation catheters, debrider, cutters, etc.) that may be useable in accordance with this invention. The devices 1002, 1004, 1006 may be radiopaque and/or may incorporate radiopaque markers such that C-arm fluoroscope 1000 may be used to image and monitor the positioning of the devices 1002, 1004, 1006 during the procedure. In addition to or, as an alternative to the use of radiographic imaging, the devices 1002, 1004, 1006 may incorporate and/or may be used in conjunction with one or more endoscopic devices, such as the typical rigid or flexible endoscopes or stereo endoscopes used by otolaryngologists during FESS procedures. Also, in addition to or as an alternative to radiographic imaging and/or endoscopic visualizations, some embodiments of the devices 1002, 1004, 1006 may incorporate sensors which enable the devices 1002, 1004, 1006 to be used in conjunction with image guided surgery systems or other electro-anatomical mapping/guidance systems including but not limited to: VectorVision (BrainLAB AG); HipNav (CASurgica); CBYON Suite (CBYON); InstaTrak, FluoroTrak, ENTrak (GE Medical); StealthStation Treon, iOn (Medtronic); Medivision; Navitrack (Orthosoft); OTS (Radionics); VISLAN (Siemens); Stryker Navigation System (Stryker Leibinger); Voyager, Z-Box (Z-Kat Inc.) and NOGA and CARTO systems (Johnson & Johnson). Commercially available interventional navigation systems can also be used in conjunction with the devices and methods. Further non-fluoroscopic interventional imaging technologies including but not limited to: OrthoPilot (B. Braun Aesculap); PoleStar (Odin Medical Technologies; marketed by Medtronic); SonoDoppler, SonoWand (MISON); CT Guide, US Guide (UltraGuide) etc. may also be used in conjunction with the devices and methods. Guidance under magnetic resonance is also feasible if the catheter is modified to interact with the system appropriately.

It is to be appreciated that the devices and methods of the present invention relate to the accessing and dilation or modification of sinus ostia or other passageways within the ear nose and throat. These devices and methods may be used alone or may be used in conjunction with other surgical or non-surgical treatments, including but not limited to the delivery or implantation of devices and drugs or other substances as described in copending U.S. patent application Ser. No. 10/912,578 entitled Implantable Devices and Methods for Delivering Drugs and Other Substances to Treat Sinusitis and Other Disorders filed on Aug. 4, 2004, issued as U.S. Pat. No. 7,361,168 on Apr. 22, 2008, the entire disclosure of which is expressly incorporated herein by reference.

Figure 2A:
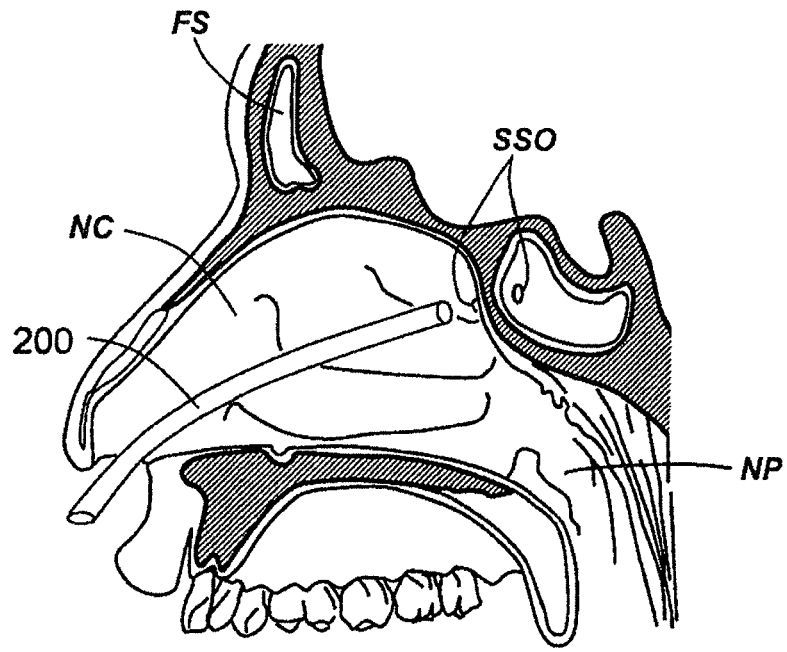
FIGS. 2A through 2D are partial sagittal sectional views through a human head showing various steps of a method for gaining access to a paranasal sinus using a guide and thereafter dilating or remodeling the ostial opening into the paranasal sinus.
Figure 2B:
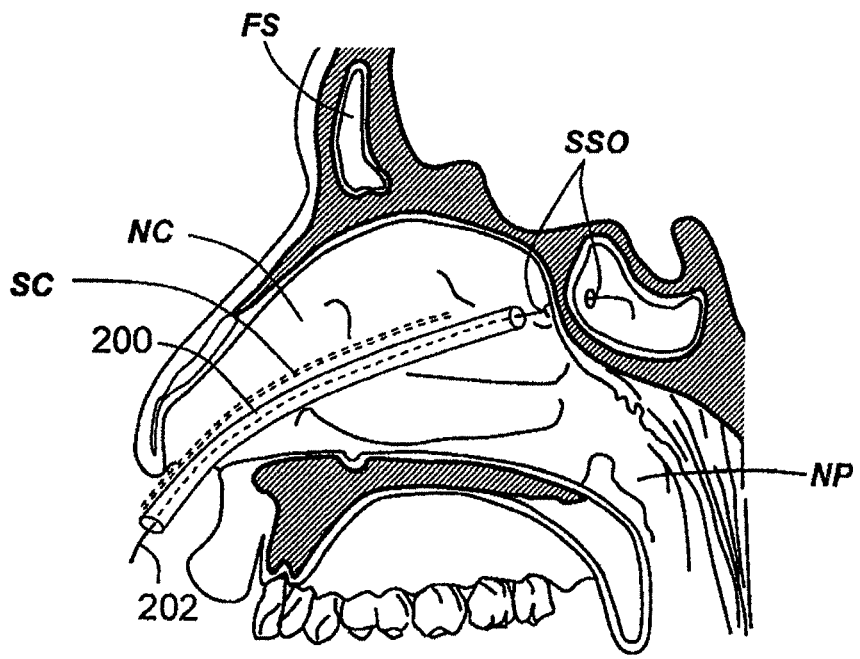
Figure 2C:
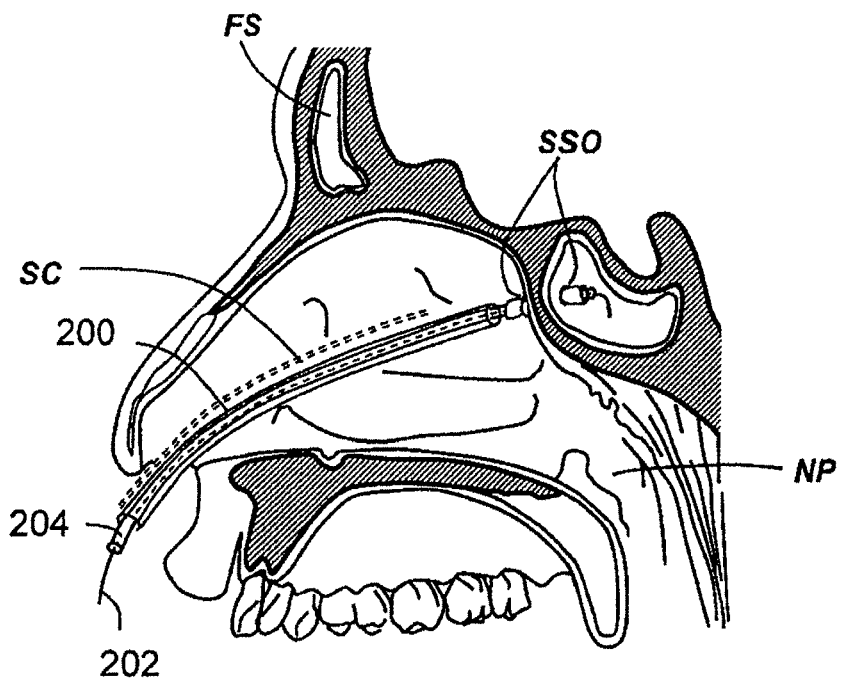
Figure 2D:
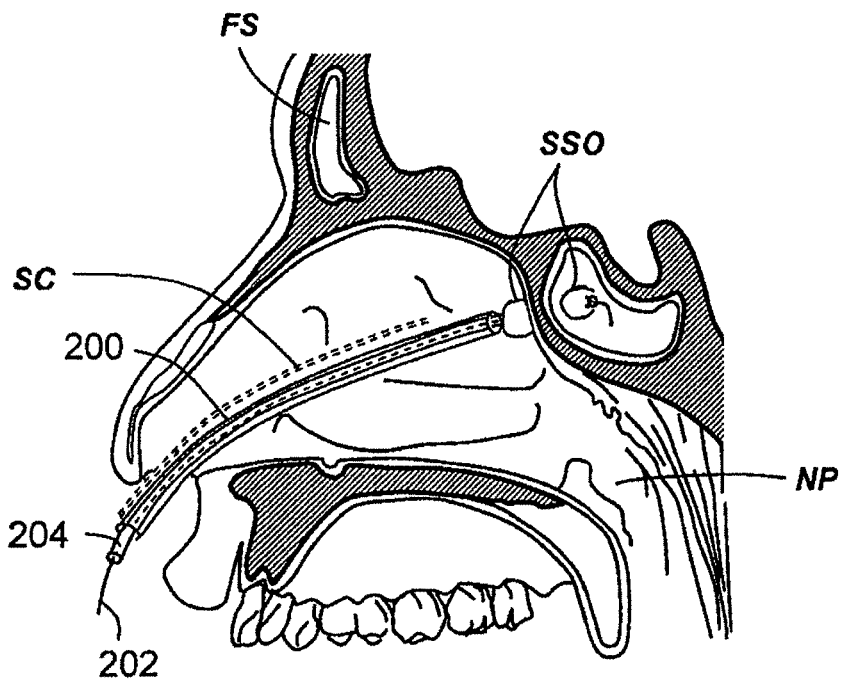

FIGS. 2A through 2D are partial sagittal sectional views through a human head showing various steps of a method of gaining access to a paranasal sinus using a guide catheter. In FIG. 2A, a first introducing device in the form of a guide catheter 200 is introduced through a nostril and through a nasal cavity NC to a location close to an ostium SSO of a sphenoid sinus SS. The guide catheter 200 may be flexible. Flexible devices are defined as devices with a flexural stiffness less than about 200 pound-force per inch over a device length of one inch. The guide catheter 200 may be straight or it may incorporate one or more preformed curves or bends. In embodiments where the guide catheter 200 is curved or bent, the deflection angle of the curve or bend may be in the range of up to 135°. Examples of specific deflection angles formed by the curved or bent regions of the guide catheter 200 are 0°, 30°, 45°, 60°, 70°, 90°, 120° and 135°. Guide catheter 200 can be constructed from suitable elements like Pebax, Polyimide, Braided Polyimide, Polyurethane, Nylon, PVC, Hytrel, HDPE, PEEK, metals like stainless steel and fluoropolymers like PTFE, PFA, FEP and EPTFE. Guide catheter 200 can have a variety of surface coatings e.g. hydrophilic lubricious coatings, hydrophobic lubricious coatings, abrasion resisting coatings, puncture resisting coatings, electrically or thermal conductive coatings, radiopaque coatings, echogenic coatings, thrombogenicity reducing coatings and coatings that release drugs. In FIG. 2B, a second introduction device comprising a guidewire 202 is introduced through the first introduction device (i.e., the guide catheter 200) so that the guidewire 202 enters the sphenoid sinus SS through the ostium SSO. Guidewire 202 may be constructed and coated as is common in the art of cardiology. In FIG. 2C, a working device 204 for example a balloon catheter is introduced over guidewire 202 into the sphenoid sinus SS. Thereafter, in FIG. 2D, the working device 204 is used to perform a diagnostic or therapeutic procedure. In this particular example, the procedure is dilation of the sphenoid sinus ostium SSO, as is evident from FIG. 2D. However, it will be appreciated that the present invention may also be used to dilate or modify any sinus ostium or other man-made or naturally occurring anatomical opening or passageway within the nose, paranasal sinuses, nasopharynx or adjacent areas. After the completion of the procedure, guide catheter 200, guidewire 202 and working device 204 are withdrawn and removed. As will be appreciated by those of skill in the art, in this or any of the procedures described in this patent application, the operator may additionally advance other types of catheters or of the present invention, a guidewire 202 may be steerable (e.g. torquable, actively deformable) or shapeable or malleable. Guidewire 202 may comprise an embedded endoscope or other navigation or imaging modalities including but not limited to fluoroscopic, X-ray radiographic, ultrasonic, radiofrequency localization, electromagnetic, magnetic, robotic and other radiative energy based modalities. In this regard, some of the figures show optional scopes SC is dotted lines. It is to be appreciated that such optional scopes SC may comprise any suitable types of rigid or flexible endoscopes and such optional scopes SC may be separate from or incorporated into the working devices and/or introduction devices of the present invention.

Figure 2E:
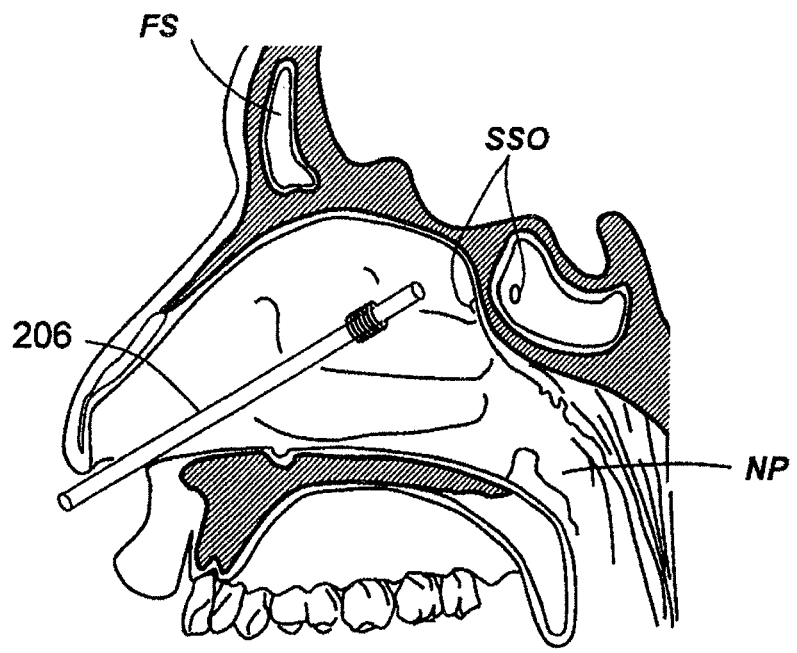
FIGS. 2E through 2H are partial sagittal sectional views through a human head showing various steps of a method for gaining access to a paranasal sinus using a steerable guide.
Figure 2F:
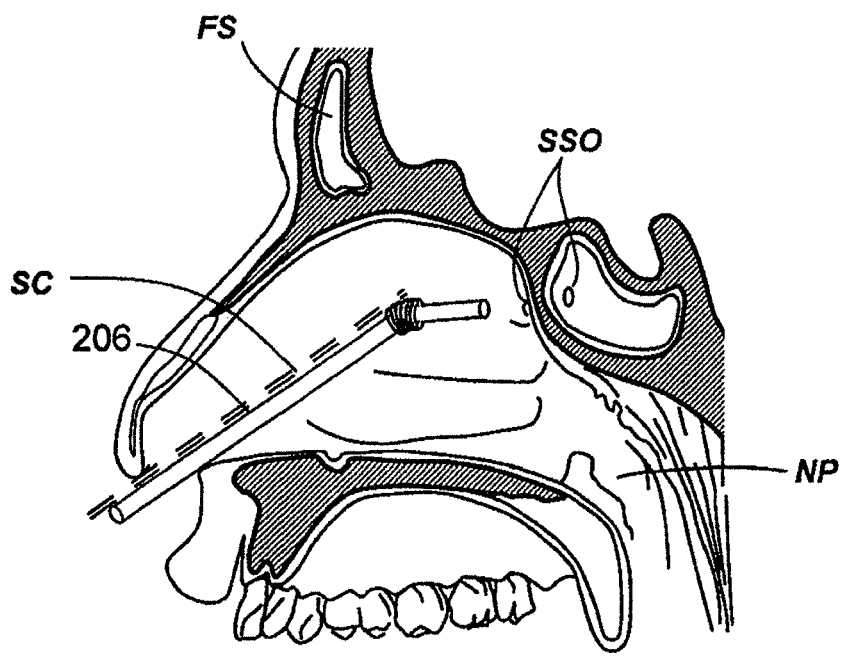
Figure 2G:
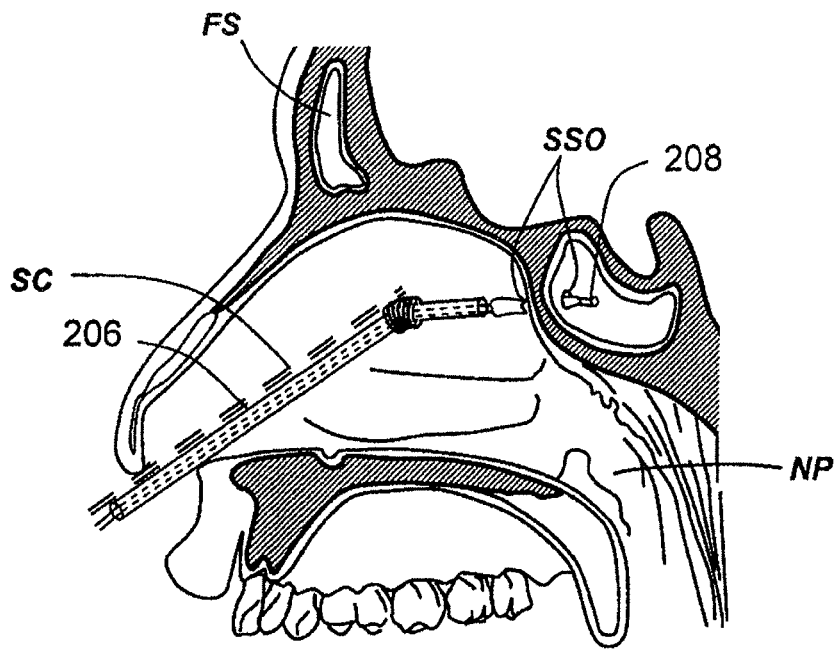
Figure 2H:
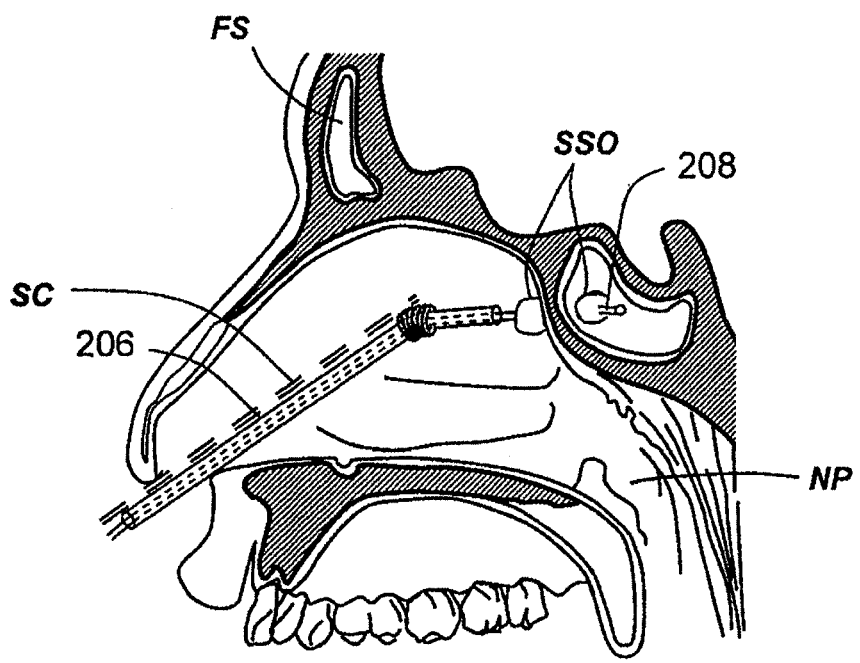

FIGS. 2E through 2H are partial sagittal sectional views through a human head showing various steps of a method of gaining access to a paranasal sinus using a steerable catheter. In FIG. 2E, an introducing device in the form of a steerable catheter 206 is introduced through a nostril. Although commercially available devices are neither designed, nor easily usable for this technique in the sinuses, examples of a device which has a steerable tip with functionality similar to that described here include but are not limited to the Naviport™ manufactured by Cardima, Inc. in Fremont, Calif.; Attain Prevail and Attain Deflectable catheters manufactured by Medtronic; Livewire Steerable Catheters manufactured by St. Jude Medical Inc.; Inquiry™ Steerable Diagnostic Catheters manufactured by Boston Scientific; TargetCath™ manufactured by EBI; Safe-Steer Catheter manufactured by Intraluminal Therapeutics, Inc.; Cynosar manufactured by Catheter Research, Inc.; Torque Control Balloon Catheter manufactured by Cordis Corp. and DynamicDeca Steerable Catheter and Dynamic XT Steerable Catheter manufactured by A.M.I. Technologies Ltd, Israel. Steerable catheter 206 comprises a proximal portion, a distal portion and a controllably deformable region between the proximal portion and the distal portion. In FIG. 2F, the steerable catheter 206 is steered through the nasal anatomy so that the distal portion of steerable catheter 206 is near an ostium SSO of a sphenoid sinus SS. In FIG. 2G, a working device in the form of a balloon catheter 208 is introduced through steerable catheter 206 so that it enters sphenoid sinus SS through the ostium SSO. Thereafter, balloon catheter 208 is adjusted so that the balloon of the balloon catheter is located in the ostium SSO. In FIG. 2H, balloon catheter 208 is used to dilate the ostium SSO. After completion of the procedure, steerable catheter 206 and balloon catheter 208 are withdrawn from the nasal anatomy. In this example, only a first introduction device in the form of a steerable catheter 206 is used to effect insertion and operative positioning of the working device (which in this example is balloon catheter 208). It will be appreciated, however, in some procedures, a second introduction device (e.g., an elongate guide member, guidewire, elongate probe, etc.) could be advanced through the lumen of the steerable catheter 206 and the working device 208 could then be advanced over such second introduction device to the desired operative location.

Figure 2I:
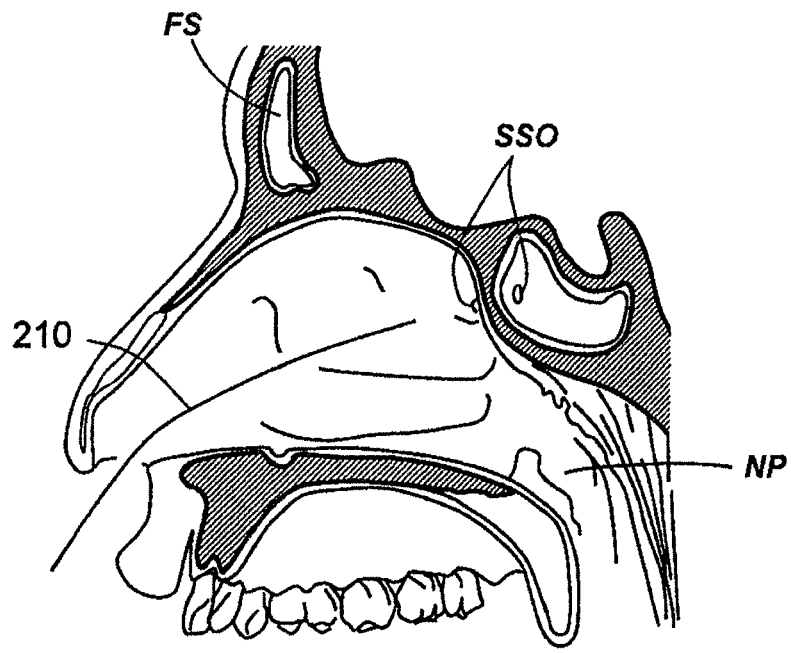
FIGS. 2I through 2L are partial sagittal sectional views through a human head showing various steps of a method for gaining access to a paranasal sinus using an introducing device in the form of a guidewire with a preset shape.
Figure 2J:
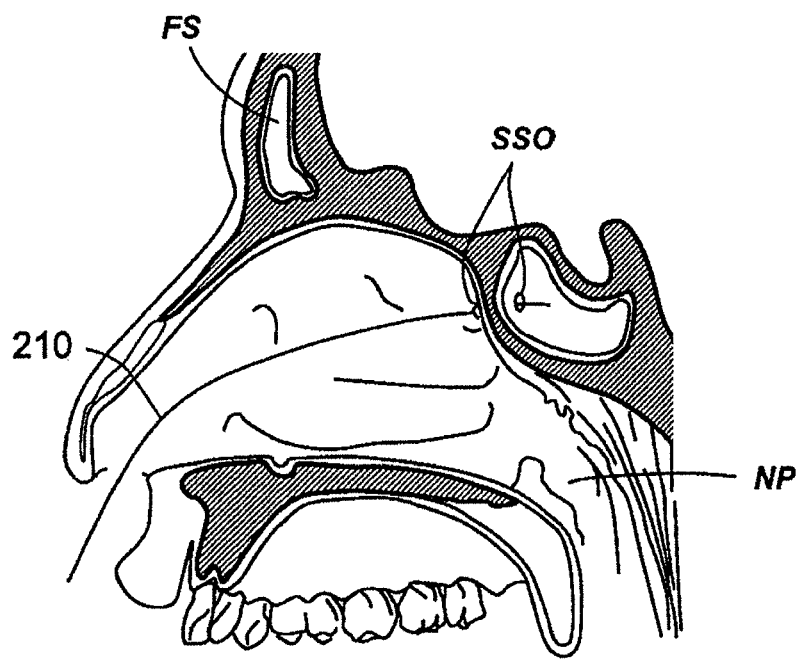
Figure 2K:
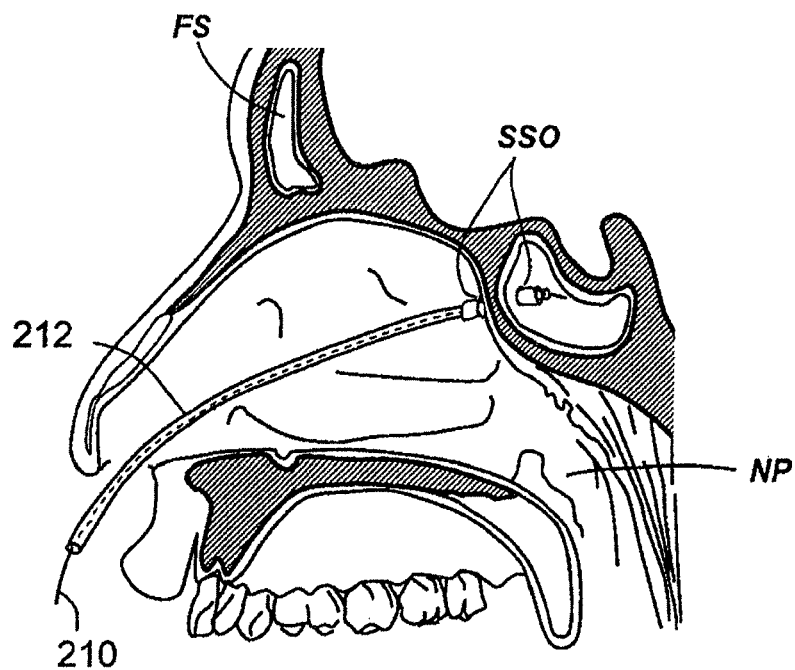
Figure 2L:
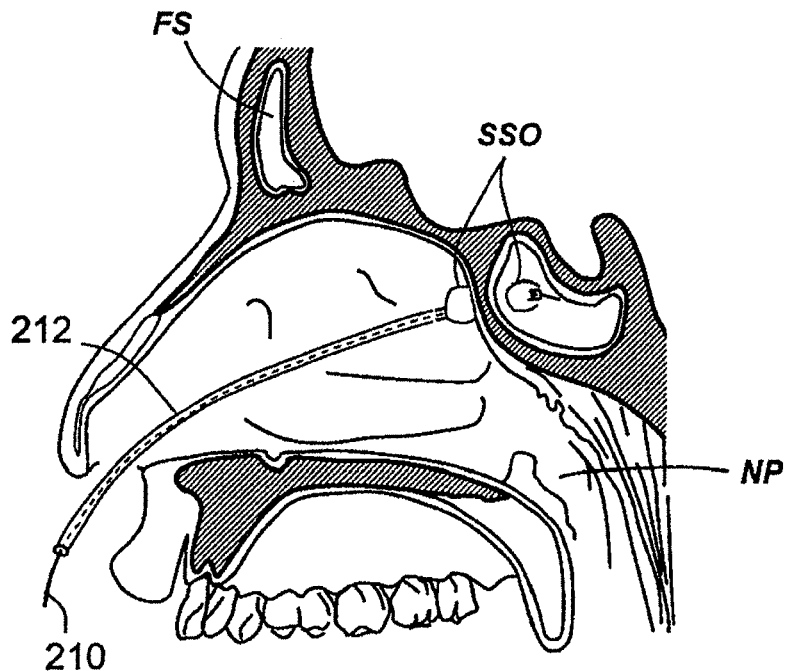

FIGS. 2I through 2L are partial sagittal sectional views through a human head showing various steps of a method for gaining access to a paranasal sinus using an introducing device in the form of a guidewire with a preset shape. In FIG. 2I, an introducing device in the form of a guidewire 210 with a preset shape is introduced in a nasal cavity. Guidewire 210 comprises a proximal portion and a distal portion and is shaped such that it can easily navigate through the nasal anatomy. In one embodiment, guidewire 210 is substantially straight. In another embodiment, guidewire 210 comprises an angled, curved or bent region between the proximal portion and the distal portion. Examples of the deflection angle of the angled, curved or bent regions are 0°, 30°, 45°, 60°, 70°, 90°, 120° and 135°. In FIG. 2J, guidewire 210 is advanced through the nasal anatomy so that the distal tip of guidewire enters a sphenoid sinus SS through an ostium SSO. In FIG. 2K, a working device in the form of a balloon catheter 212 is advanced along guidewire 210 into the sphenoid sinus SS. Typically, as described more fully herebelow, the working device will have a guidewire lumen extending through or formed in or on at least a portion of the working device 212 to facilitate advancement of the working device 212 over the guidewire 212 in the manner well understood in the art of interventional medicine. Thereafter, the position of balloon catheter 212 is adjusted so that the balloon of the balloon catheter is located in the ostium SSO. As described elsewhere in this application, the balloon catheter 212 may be radiopaque and/or may incorporate one or more visible or imageable markers or sensors. In FIG. 2L, balloon catheter 212 is used to dilate the ostium SSO. After completion of the procedure, guidewire 210 and balloon catheter 212 are withdrawn from the nasal anatomy. In one embodiment, balloon catheter 212 is shapeable or malleable.

Figure 2M:
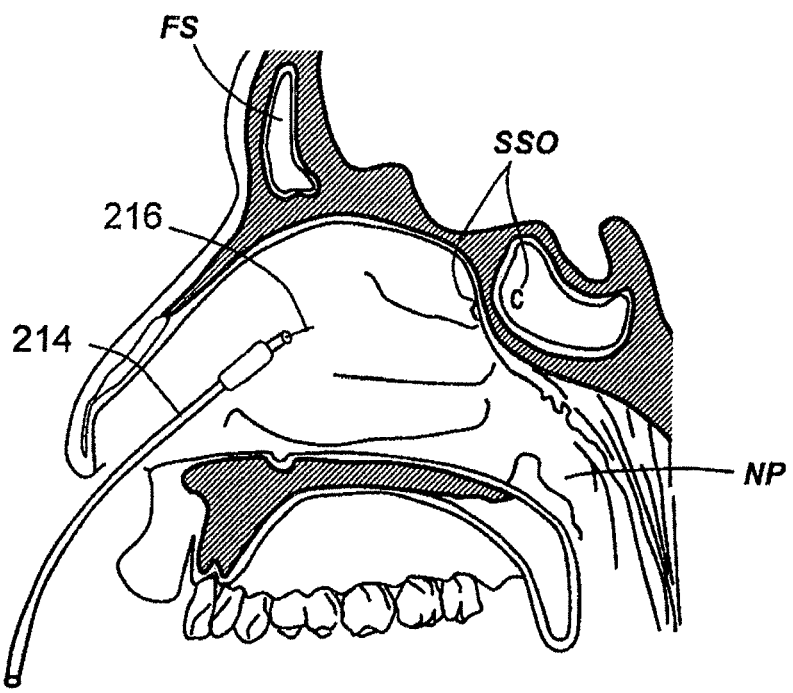
FIGS. 2M through 2O are partial sagittal sectional views through a human head showing various steps of a method for gaining access to a paranasal sinus using a balloon catheter that has a guide protruding from its distal end.
Figure 2N:
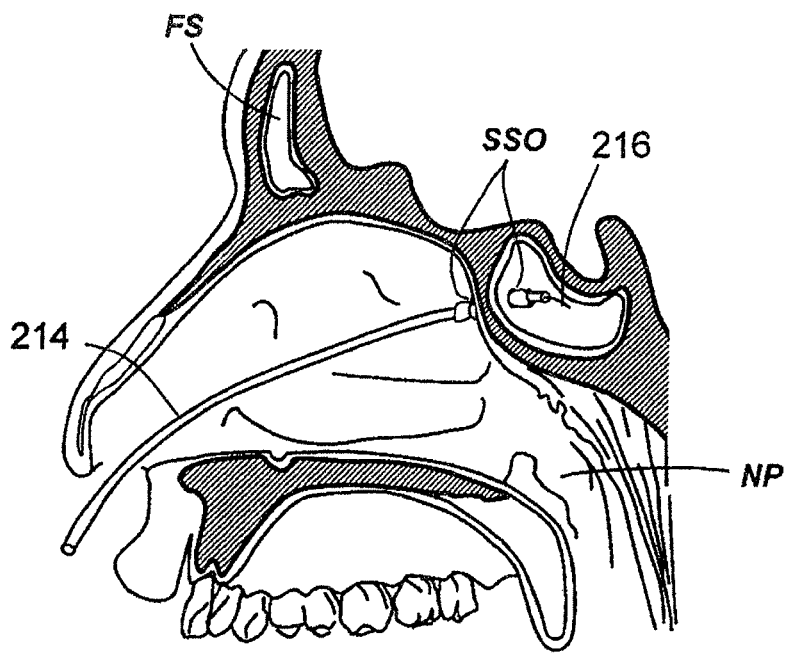
Figure 2O:
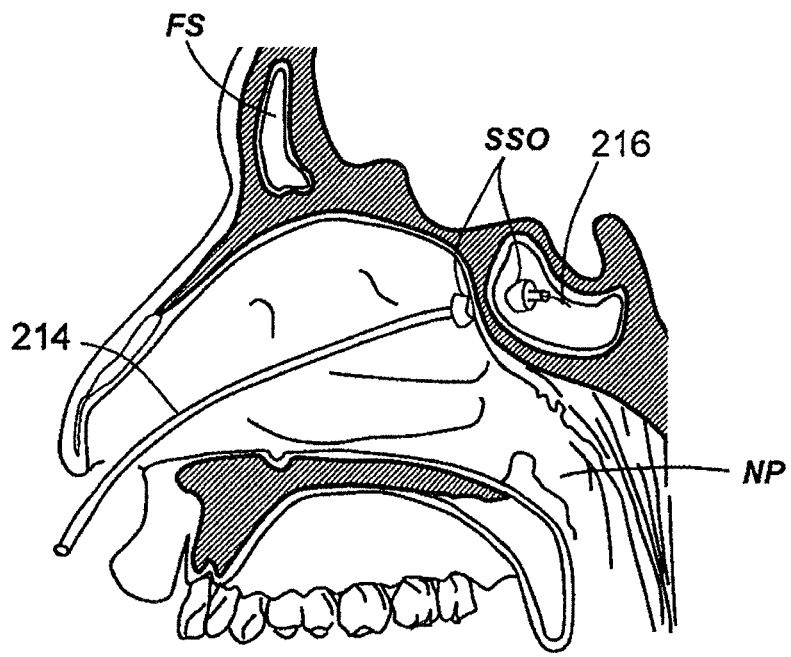

FIGS. 2M through 2O are partial sagittal sectional views through a human head showing various steps of a method of gaining access to a paranasal sinus using a balloon catheter comprising a steering wire at its distal end. In FIG. 2M, a working device comprising a balloon catheter 214 comprising a proximal portion and distal portion is introduced in a nasal cavity. Balloon catheter 214 comprises a steering wire 216 at its distal end. In FIG. 2N, balloon catheter 214 is advanced through the nasal anatomy into a sphenoid sinus SS through a sphenoid sinus ostium SSO. Thereafter, the position of balloon catheter 214 is adjusted so that the balloon of the balloon catheter is located in the ostium SSO. In FIG. 2O, balloon catheter 214 is used to dilate the ostium SSO. After completion of the procedure, balloon catheter 214 is withdrawn from the nasal anatomy. In one embodiment, steering wire 216 can be retracted into or advanced from balloon catheter 214. The retraction or advancement of steering wire can be controlled by several means like a thumb wheel, a slide, a button hooked up to electronic motor and a trigger. In another embodiment, steering wire 216 may be hollow or may incorporate one or more lumen(s) to enable it to introduce or remove devices or diagnostic or therapeutic agents, examples of which are described in copending U.S. patent application Ser. No. 10/912,578 entitled Implantable Devices and Methods for Delivering Drugs and Other Substances to Treat Sinusitis and Other Disorders filed on Aug. 4, 2004, issued as U.S. Pat. No. 7,361,168 on Apr. 22, 2008, the entire disclosure of which is expressly incorporated herein by reference.

Figure 2P:
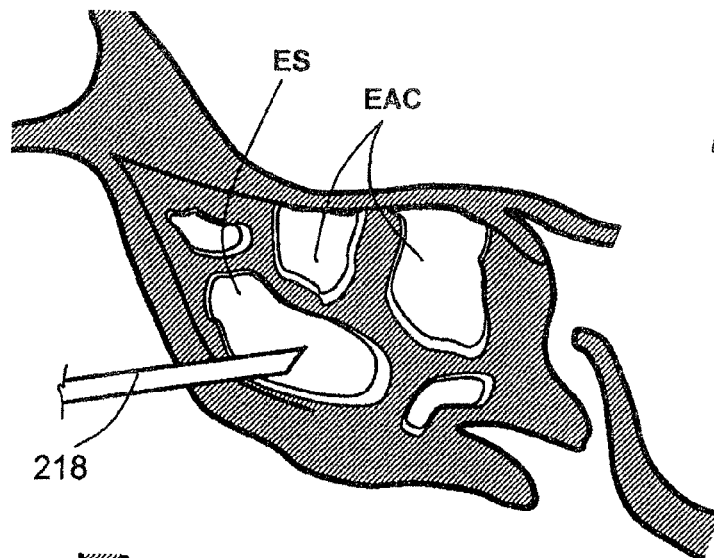
FIGS. 2P through 2X are partial sagittal sectional views through a human head showing various steps of a method of accessing an ethmoid sinus through a natural or artificially created opening of the ethmoid sinus.
Figure 2Q:
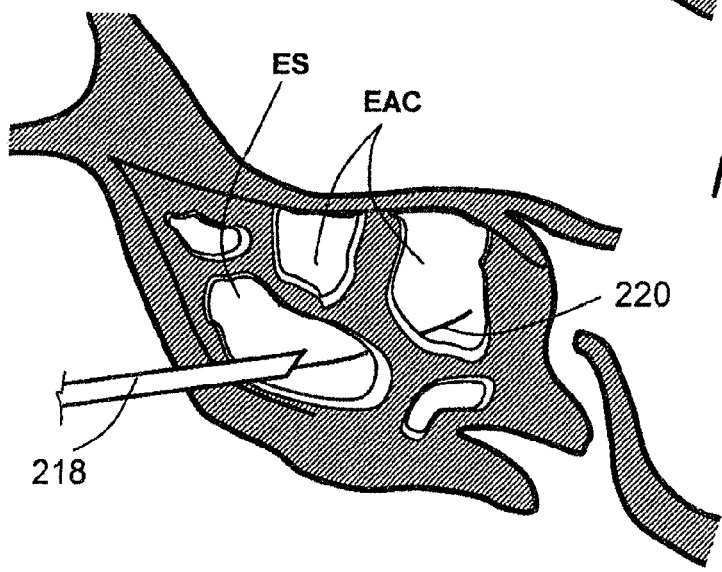
Figure 2R:
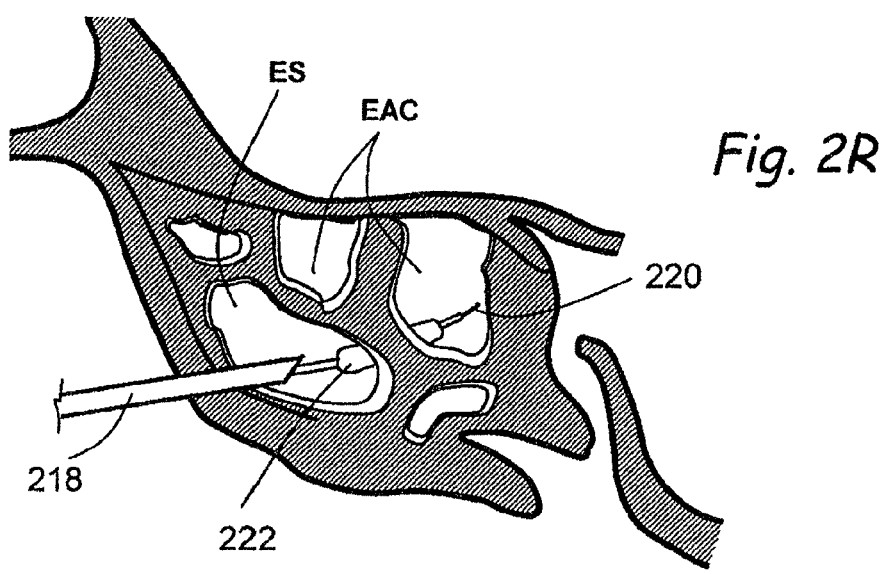
Figure 2S:
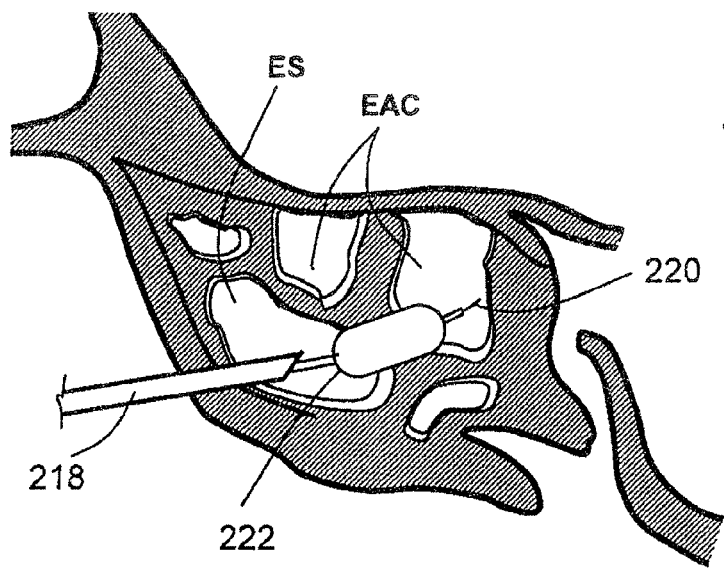
Figure 2T:
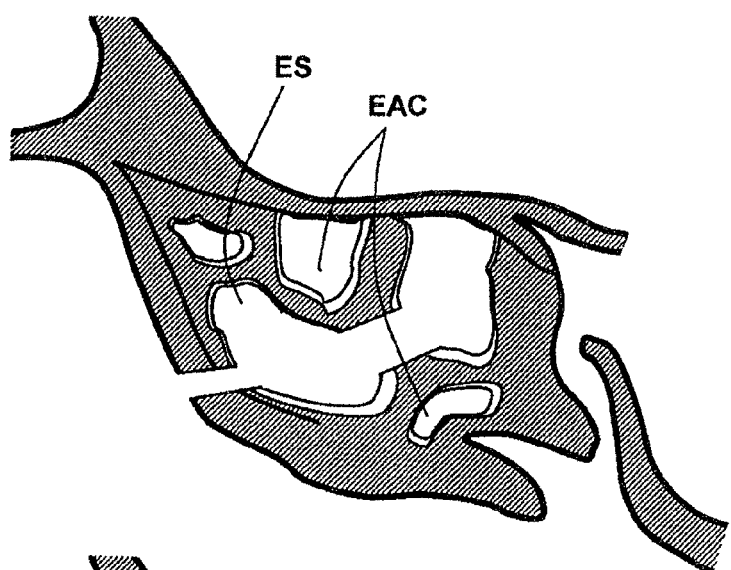
Figure 2U:
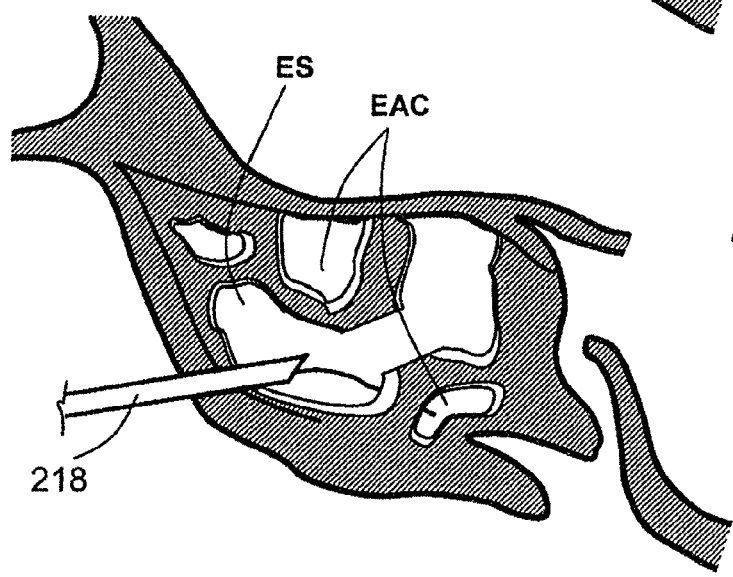
Figure 2V:
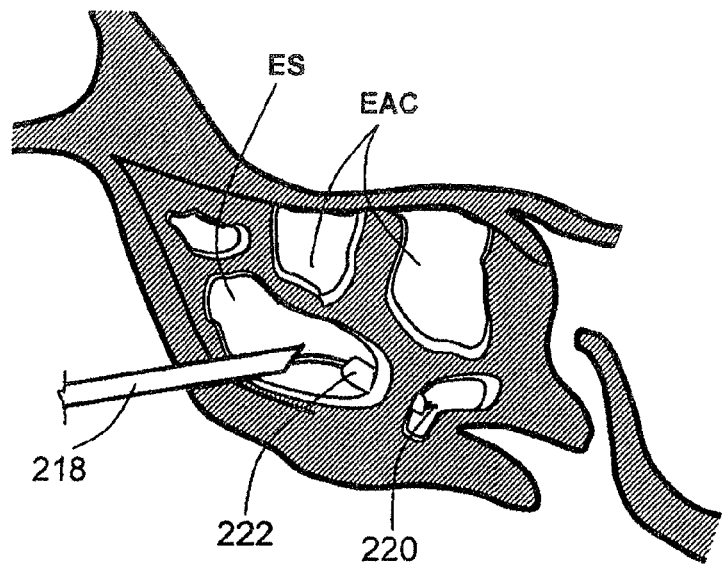
Figure 2W:
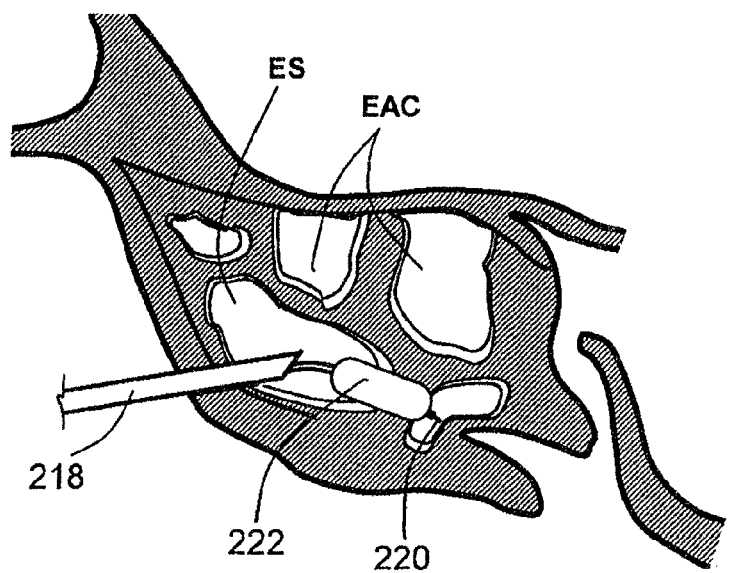
Figure 2X:
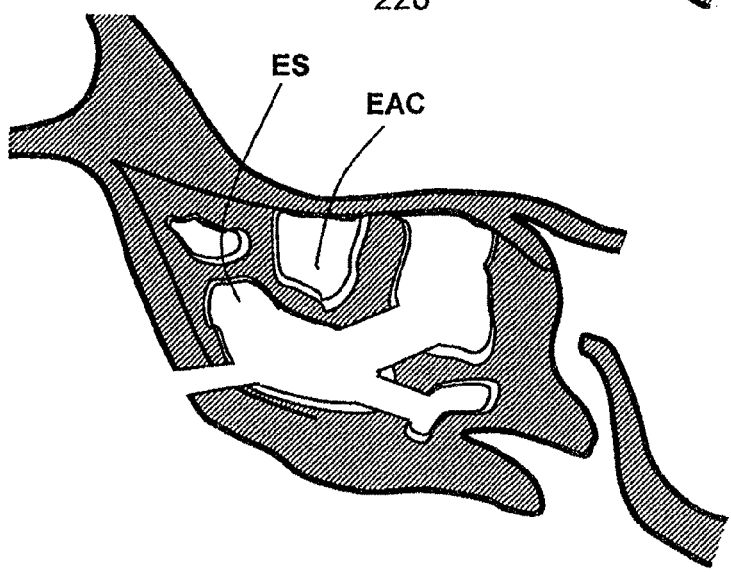

FIGS. 2P through 2X are partial sagittal sectional views through a human head showing various steps of a method for accessing an ethmoid sinus through a natural or artificially created opening of the ethmoid sinus. In FIG. 2P, an introducing device in the form of a guide catheter 218 is introduced in an ethmoid sinus ES. Ethmoid sinus ES comprises multiple ethmoid air cells EAC. In FIG. 2Q, a guidewire 220 is introduced through guide catheter into a first EAC. Thereafter, in FIG. 2R, a balloon catheter 222 is introduced over guidewire 220 into the first EAC. In FIG. 2S, balloon catheter 222 is inflated to dilate the structures of ES. In FIG. 2T, guide catheter 218, guidewire 220 and balloon catheter 222 are withdrawn leaving a first new passage in the ES. The newly created passage in the ES facilitates drainage of the mucous through the ES. Alternatively, in FIG. 2U, only balloon catheter 222 is withdrawn. The position of guide catheter 218 is adjusted and guidewire 220 is introduced into a second EAC. In FIG. 2V, balloon catheter 222 is introduced over guidewire 220 into the second EAC. In FIG. 2W, balloon catheter 222 is inflated to dilate the structures of ES. In FIG. 2X, guide catheter 218, guidewire 220 and balloon catheter 222 are withdrawn leaving a second new passage in the ES. The second new passage in the ES further facilitates drainage of the mucous through the ES. This method of dilating the structures of ES can be repeated to create multiple new passages in the ES.

Figure 2Y:
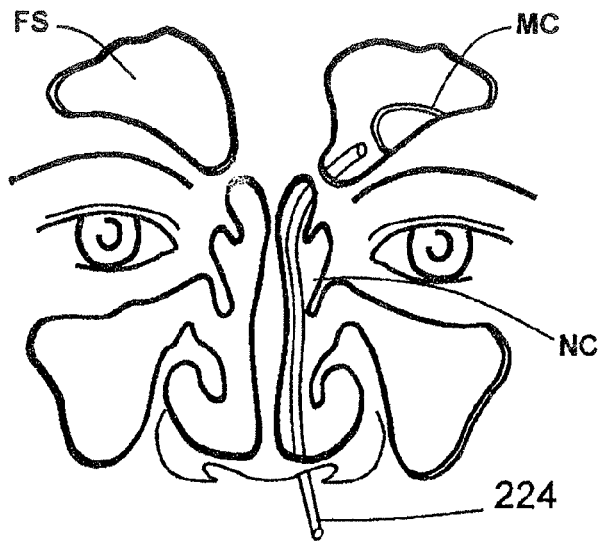
Figure 2Z:
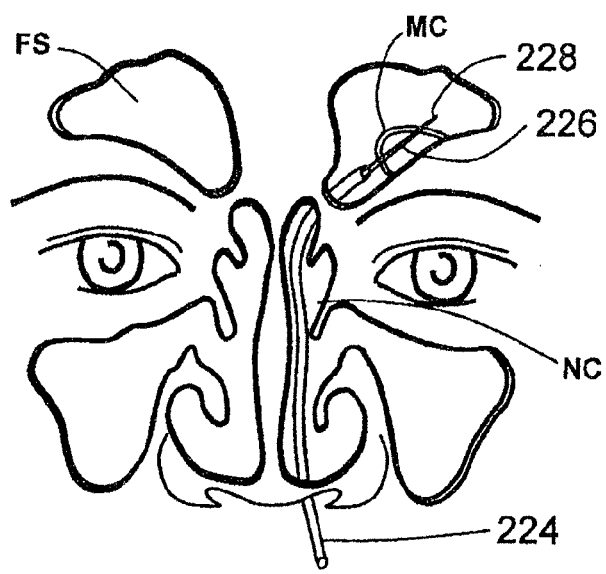
Figure 2A:
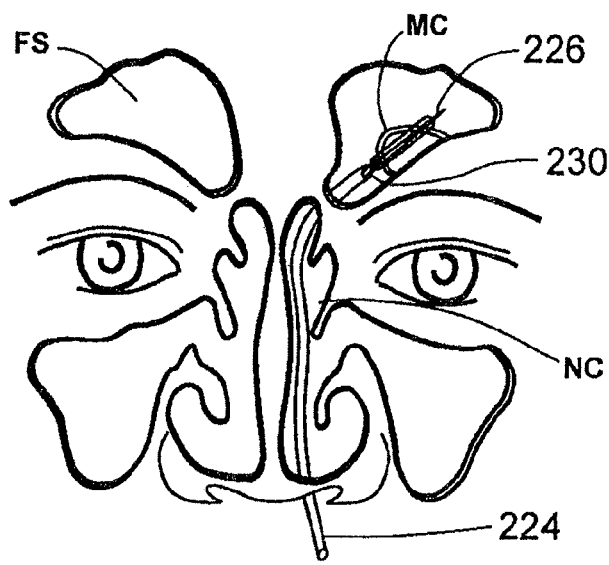
Figure 2A:
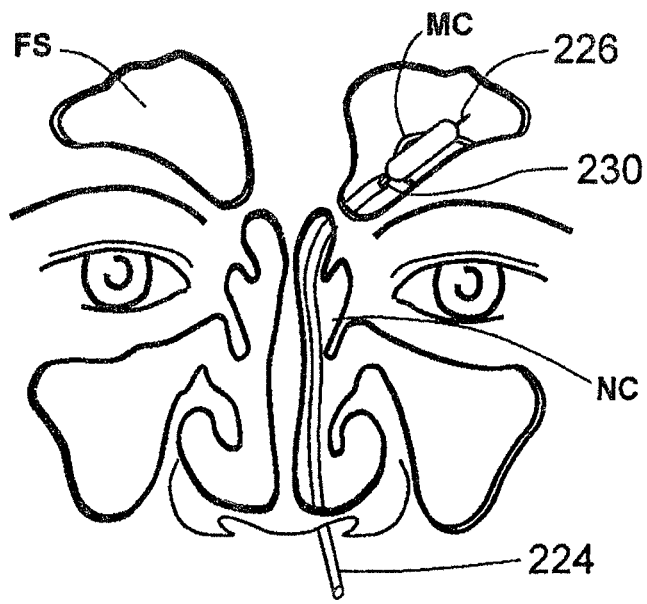
Figure 2A:
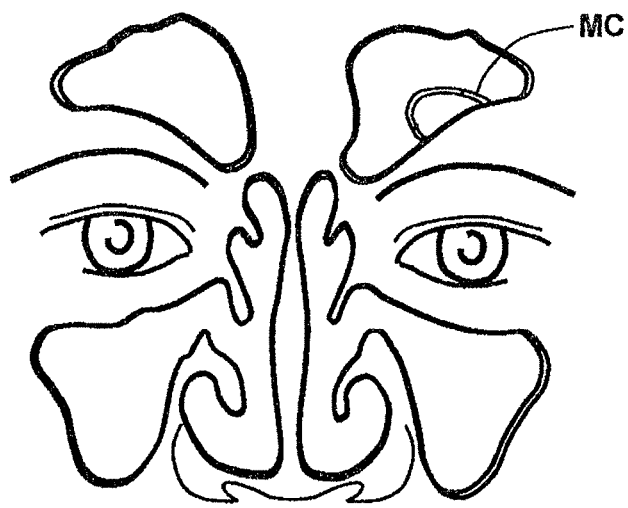

FIGS. 2Y through 2AC are partial coronal sectional views through a human head showing various steps of a method for treating a mucocele in a frontal sinus. In FIG. 2Y, an introducing device in the form of a guide catheter 224 is introduced in a frontal sinus FS through the nasal cavity NC. Frontal sinus FS has a mucocele MC to be treated. In FIG. 2Z, a penetrating device 226 comprising a sharp tip 228 is introduced through guide catheter 224 such that penetrating device 226 punctures the MC at least partially. In FIG. 2AA, a balloon catheter 230 is introduced over penetrating device 226 into the MC. Thereafter, in FIG. 2AB, balloon catheter 230 is inflated to rupture the MC and allow the drainage of contents of the MC. In FIG. 2AC, penetrating device 226 and balloon catheter 230 are withdrawn.

The methods disclosed herein may also comprise the step of cleaning or lavaging anatomy within the nose, paranasal sinus, nasopharynx or nearby structures including but not limited to irrigating and suctioning. The step of cleaning the target anatomy can be performed before or after a diagnostic or therapeutic procedure.

The methods of the present invention may also include one or more preparatory steps for preparing the nose, paranasal sinus, nasopharynx or nearby structures for the procedure, such as spraying or lavaging with a vasoconstricting agent (e.g., 0.025-0.5% phenylephyrine or Oxymetazoline hydrochloride (Neosynephrine or Afrin) to cause shrinkage of the nasal tissues, an antibacterial agent (e.g., provodine iodine (Betadine), etc. to cleanse the tissues, etc.

Figure 3A:
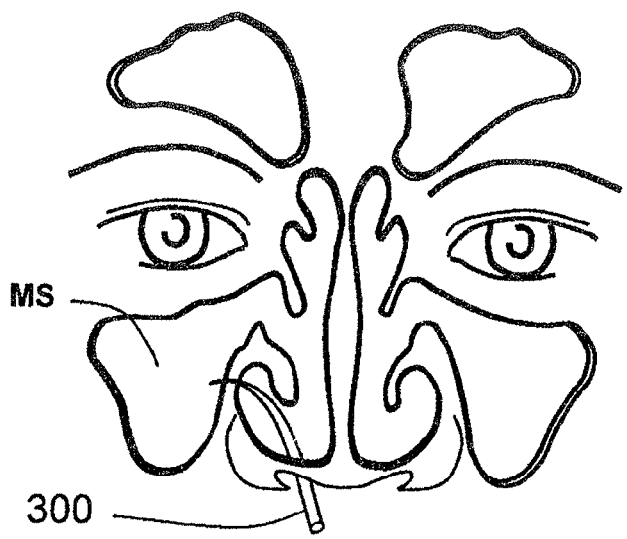
FIGS. 3A through 3C are partial coronal sectional views through a human head showing various steps of a method of accessing a paranasal sinus through an artificially created opening of the paranasal sinus.
Figure 3B:
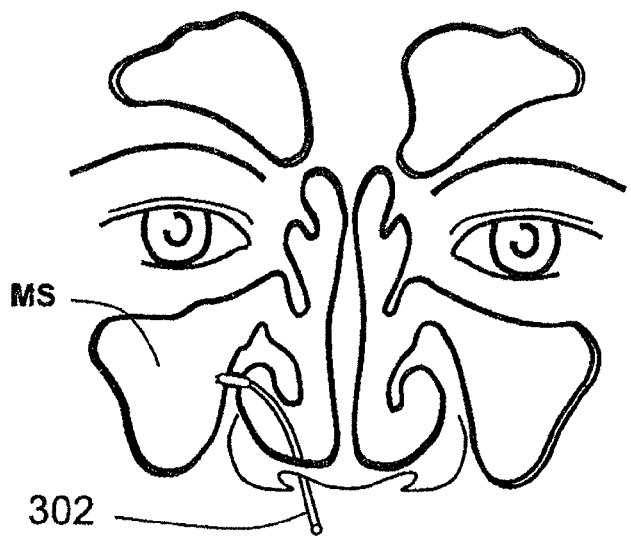
Figure 3C:
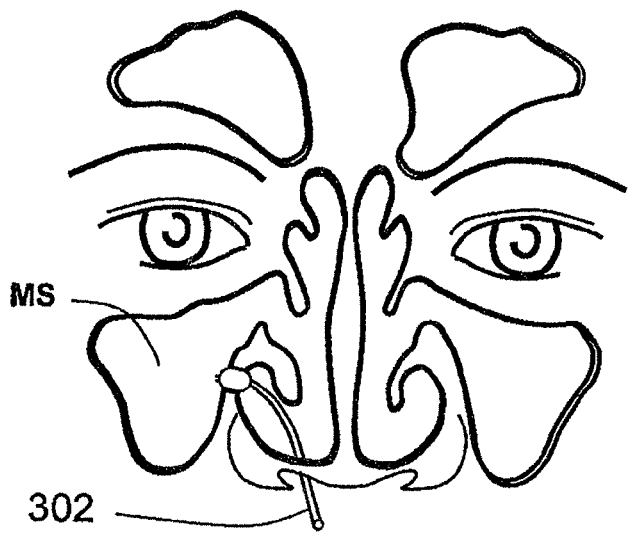

FIGS. 3A through 3C are partial coronal sectional views through a human head showing various steps of a method of accessing a paranasal sinus through an artificially created opening of the paranasal sinus. In FIG. 3A, a puncturing device 300 is inserted through a nostril and used to create an artificial opening in a maxillary sinus. There are several puncturing devices well known in the art like needles including needles, needles with bent shafts, dissectors, punches, drills, corers, scalpels, burs, scissors, forceps and cutters. In FIG. 3B, puncturing device 300 is withdrawn and a working device for example a balloon catheter 302 is introduced through the artificial opening into the maxillary sinus. In FIG. 3C, balloon catheter 302 is used to dilate the artificially created opening in the maxillary sinus. After this step, the balloon catheter 302 is withdrawn. It will be appreciated that, in some embodiments, the puncturing device 300 may have a lumen through which an introduction device (e.g., a guidewire or other elongate probe or member), may be inserted into the maxillary sinus and the puncturing device 300 may then be removed leaving such introduction device (e.g., a guidewire or other elongate probe or member) in place. In such cases, the working device (e.g., balloon catheter 302) may incorporate a lumen or other structure that allows the working device (e.g., balloon catheter 300) to be advanced over the previously inserted introduction device (e.g., a guidewire or other elongate probe or member).

Figure 4A:
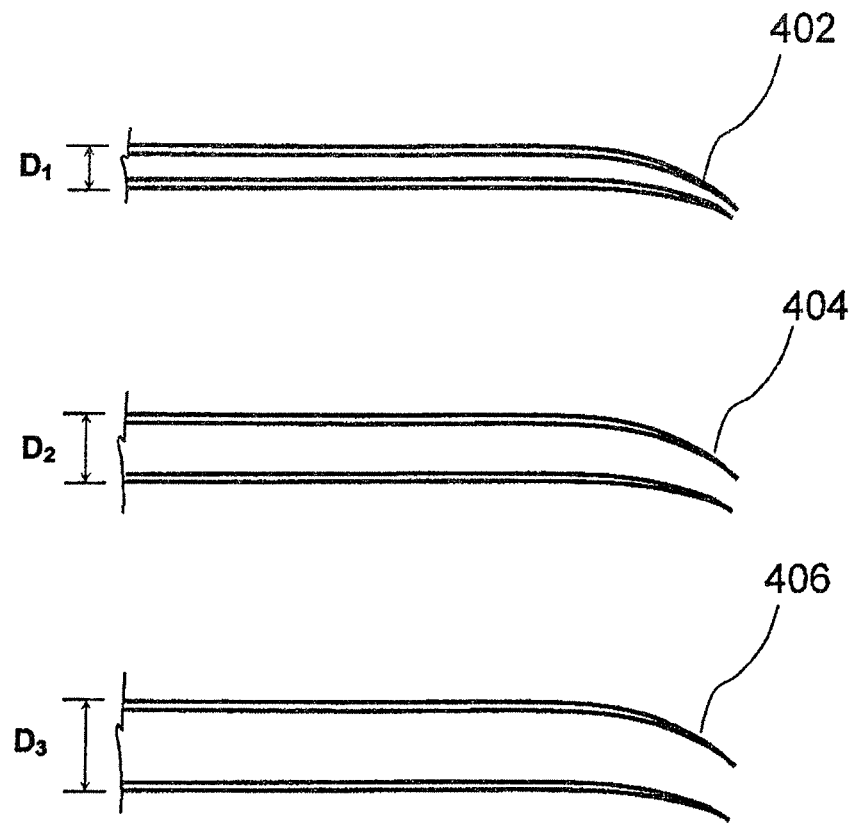
FIG. 4A shows a partial longitudinal sectional view of a system for dilating a sinus ostium or other intranasal anatomical structure, such system comprising three progressively larger dilators useable in sequence.

In the methods illustrated so far, balloon catheters were used only as an example for the several alternate working devices that could be used with this invention. FIG. 4A shows a sectional view of an example of a working device comprising a set of three sequential dilators: a first sequential dilator 402, a second sequential dilator 404 and a third sequential dilator 406. The D3 of third sequential dilator 406 is greater than the diameter D2 of second sequential dilator 404 which in turn is greater than the diameter D1 of first sequential dilator 402. The sequential dilators may comprise one or more bent or angled regions. The sequential dilators can be constructed from a variety of biocompatible materials like stainless steel 316. A variety of other metals, polymers and materials can also be used to construct the sequential dilators.

Figure 4B:
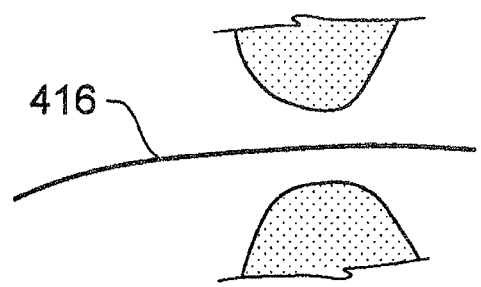
FIGS. 4B through 4E show various steps of a method of dilating a nasal cavity using a working device comprising a balloon catheter with a pressure-expandable stent.
Figure 4C:
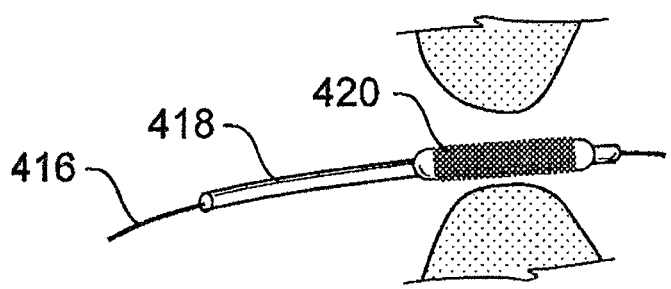
Figure 4D:
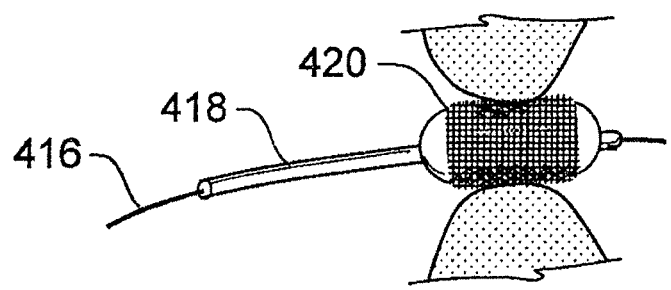
Figure 4E:
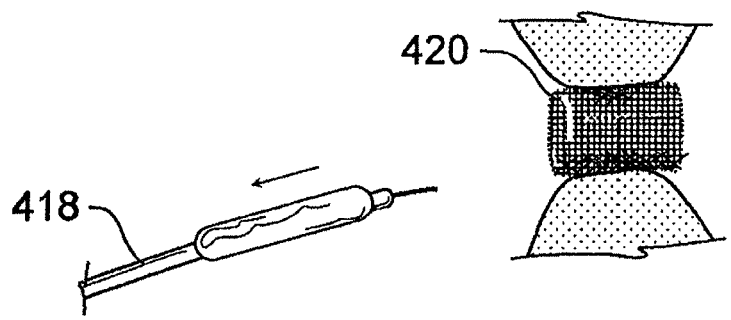

FIGS. 4B through 4E show various steps of a method of dilating a nasal cavity using a working device comprising a balloon catheter with a pressure-expandable stent. In FIG. 4B, an introducing device e.g. a guidewire 416 is introduced into a nasal cavity e.g. an ostium of a sinus. In FIG. 4C, a balloon catheter 418 is introduced over guidewire 416 into the nasal cavity. Balloon catheter 418 comprises a pressure-expandable stent 420. The position of balloon catheter 418 is adjusted so that pressure-expandable stent 420 is located substantially within the target anatomy where the stent is to be deployed. In FIG. 4D, the balloon of balloon catheter 418 is expanded to deploy pressure-expandable stent 420. In FIG. 4E, balloon catheter 418 is withdrawn leaving pressure-expandable stent 420 in the nasal cavity. Several types of stent designs can be used to construct stent 420 like metallic tube designs, polymeric tube designs, chain-linked designs, spiral designs, rolled sheet designs, single wire designs etc. These designs may have an open celled or closed celled structure. A variety of fabrication methods can be used for fabricating stent 420 including but not limited to laser cutting a metal or polymer element, welding metal elements etc. A variety of materials can be used for fabricating stent 420 including but not limited to metals, polymers, foam type materials, plastically deformable materials, super elastic materials etc. Some non-limiting examples of materials that can be used to construct the stent are silicones e.g. silastic, polyurethane, gelfilm and polyethylene. A variety of features can be added to stent 420 including but not limited to radiopaque coatings, drug elution mechanisms etc.

Figure 4F:
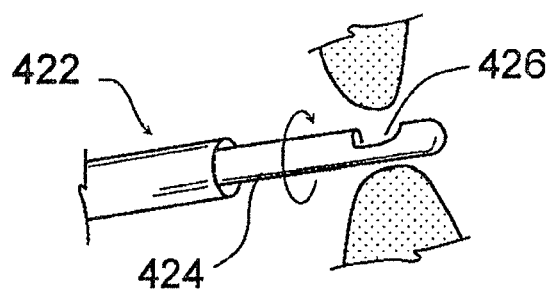
FIG. 4F shows a partial perspective view of a working device that comprises a side suction and/or side cutter.

FIG. 4F shows a partial perspective view of an embodiment of a working device comprising a side suction and/or cutting device 422 comprising a device body 424 having a side opening 426. Cutting device 422 is advanced into a passageway such as a nostril, nasal cavity, meatus, ostium, interior of a sinus, etc. and positioned so that side opening 426 is adjacent to matter (e.g., a polyp, lesion, piece of debris, tissue, blood clot, etc.) that is to be removed. Cutting device 422 is rotated to cut tissue that has been positioned in the side opening 426. Cutting device 422 may incorporate a deflectable tip or a curved distal end which may force side opening 426 against the tissue of interest. Further, this cutting device 422 may have an optional stabilizing balloon incorporated on one side of cutting device 422 to press it against the tissue of interest and may also contain one or more on-board imaging modalities such as ultrasound, fiber or digital optics, OCT, RF or electro-magnetic sensors or emitters, etc.

Figure 4G:
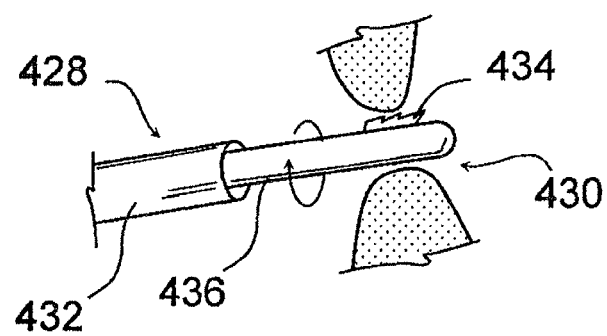
FIG. 4G shows a partial perspective view of a working device that comprises a rotating cutter to cut away tissue.

FIG. 4G shows a partial perspective view of an embodiment of a working device comprising a rotating cutter device to cut away tissue. Rotating cutter device 428 comprises a rotating member 430 enclosed in an introducing device 432. Rotating member 430 comprises a rotating blade 434 located near the distal region of rotating member 430. Rotating blade 434 may be retractable into rotating member 430. Rotating cutter device 428 is inserted in a passageway 436 such as a nostril, nasal cavity, meatus, ostium, interior of a sinus, etc. and positioned so that rotating blade 434 is adjacent to matter (e.g., a polyp, lesion, piece of debris, tissue, blood clot, etc.) that is to be removed. Thereafter, rotating member 430 is rotated to cause rotating blade 434 to remove tissue. In one embodiment, rotating member 430 can be retracted into introducing device 432. In another embodiment, rotating cutter device 428 may comprise a mechanism for suction or irrigation near the distal end of rotating cutter device 428.

Figure 4H:
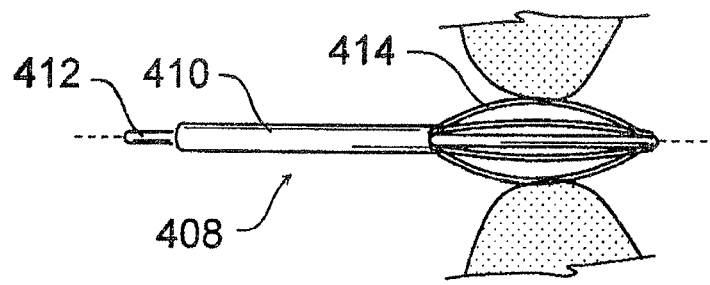
FIGS. 4H and 4I show various steps of a method of dilating the ostium of a paranasal sinus or other nasal passageway using a mechanical dilator.
Figure 4I:
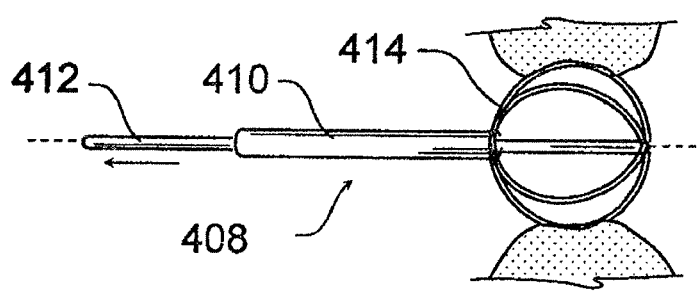

FIGS. 4H and 4I show various steps of a method of dilating a nasal cavity using a working device comprising a mechanical dilator 408. Mechanical dilator 408 comprises an outer member 410, an inner member 412 and one or more elongate bendable members 414. Inner member 412 can slide within outer member 410. The proximal ends of bendable members 414 are attached to distal end of outer member 410 and the distal ends of bendable members 414 are attached to distal end of inner member 412. In FIG. 4H, mechanical dilator 408 is inserted into an opening in the nasal anatomy e.g. an ostium of a sinus. Mechanical dilator 408 is positioned in the opening such that bendable members 414 are within the opening in the nasal anatomy. In FIG. 4I, relative motion of outer member 410 and inner member 412 causes the distal end of outer member 410 to come closer to the distal end of inner member 412. This causes bendable members 414 to bend such that the diameter of the distal region of mechanical dilator 408 increases. This causes bendable members 414 to come into contact with the opening in the nasal anatomy and exert an outward pressure to dilate the opening. Various components of mechanical dilator 408 like outer member 410, inner member 412 and bendable members 414 can be constructed from suitable biocompatible materials like stainless steel 316. A variety of other metals, polymers and materials can also be used to construct the various components of mechanical dilator 408. In one embodiment, outer member 410 is substantially rigid and inner member 412 is flexible. Outer member 410 can be substantially straight or may comprise one or more bent or angled regions. Inner member 412 may comprise one or more lumens.

Figure 4J:
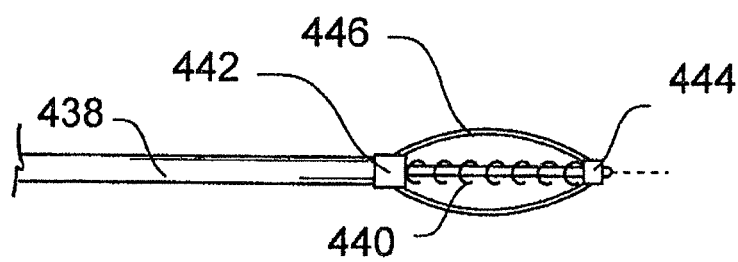
FIGS. 4J and 4K show perspective views of a mechanical dilator comprising a screw mechanism.
Figure 4K:
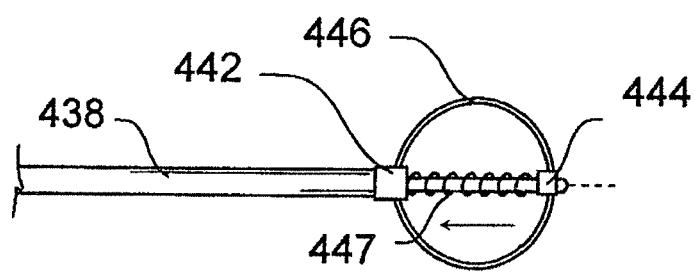

FIGS. 4J and 4K illustrate a perspective view of a design of a mechanical dilator comprising a screw mechanism. FIG. 4J shows the mechanical dilator comprising an outer member 438 and an inner screw member 440. Inner screw member 440 is connected to outer member 438 through a first pivot 442 located on the distal end of outer member 438. The distal end of inner screw member 440 is connected to a second pivot 444. The mechanical dilator further comprises one or more bendable members 446. The distal end of bendable members 446 is attached to second pivot 444 and the proximal end of bendable members 446 is attached to first pivot 442. In FIG. 4K, inner screw member 440 is rotated in one direction. This causes second pivot 444 to come closer to first pivot 442. This causes bendable members 446 to bend in the radial direction exerting an outward radial force. This force can be used to dilate or displace portions of the anatomy. Outer member 438 can be substantially straight or may comprise one or more bent or angled regions. Inner screw member 440 may comprise one or more lumens.

FIGS. 4L and 4M illustrate sectional views of a design of a mechanical dilator comprising a pushable member. FIG. 4L shows the mechanical dilator comprising an outer member 448 comprising one or more bendable regions 449 on the distal end of outer member 448. Mechanical dilator further comprises an inner pushable member 450 comprising an enlarged region 452 on the distal end of inner pushable member 450. In FIG. 4M, inner pushable member 450 is pushed in the distal direction. This exerts an outward force on bendable regions 449 causing bendable regions 449 to bend in a radial direction exerting an outward force. This force can be used to dilate or displace portions of the anatomy. Outer member 448 can be substantially straight or may comprise one or more bent or angled regions. Inner pushable member 450 may comprise one or more lumens.

FIGS. 4N and 4O illustrate sectional views of a design of a mechanical dilator comprising a pullable member. FIG. 4N shows the mechanical dilator comprising an outer member 454 comprising one or more bendable regions 456 on the distal end of outer member 454. Mechanical dilator further comprises an inner pullable member 458 comprising an enlarged region 460 on the distal end of inner pullable member 458. In FIG. 4O, inner pullable member 458 is pulled in the proximal direction. This exerts an outward force on bendable regions 456 causing bendable regions 456 to bend in a radial direction exerting an outward force. This force can be used to dilate or displace portions of the anatomy. Outer member 454 can be substantially straight or may comprise one or more bent or angled regions. Inner pullable member 458 may comprise one or more lumens.

FIGS. 4P and 4Q illustrate sectional views of a design of a mechanical dilator comprising a hinged member. FIG. 4P shows the mechanical dilator comprising an outer member 462 comprising one or more bendable regions 464 located on the distal end of outer member 462. The mechanical dilator also comprises an inner member 466 located within outer member 462. In one embodiment, inner member 466 is tubular. The distal end of inner member 466 comprises one or more first hinges 468. First hinges 468 are hinged to the proximal ends of one or more moving elements 470. Distal ends of moving elements 470 are hinged to one or more second hinges 472 located on the inner surface of outer member 462. In FIG. 4Q, inner member 466 is pushed in the distal direction. This causes moving elements 470 to exert an outward radial force on bendable regions 464 causing bendable regions 464 to bend in an outward radial direction with an outward force. This outward force can be used to dilate or displace portions of the anatomy. Outer member 462 can be substantially straight or may comprise one or more bent or angled regions. Inner member 466 may comprise one or more lumens.

Figure 4S:
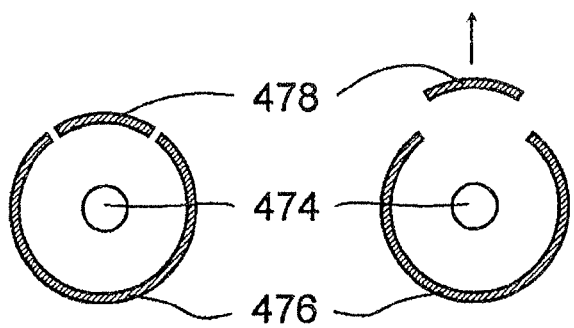
Figure 4S:
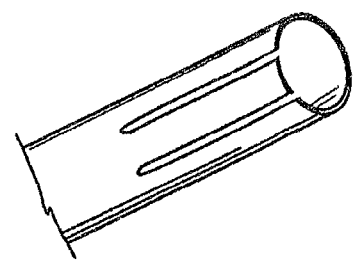
Figure 4U:
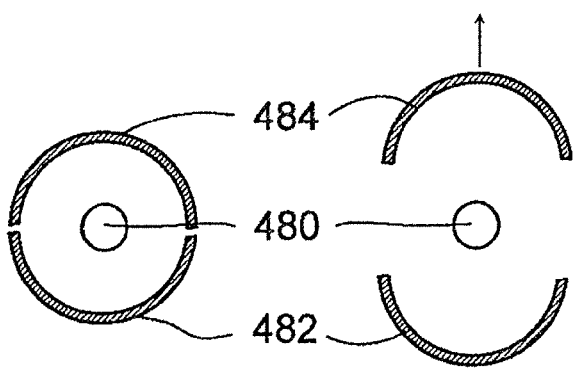
Figure 4U:
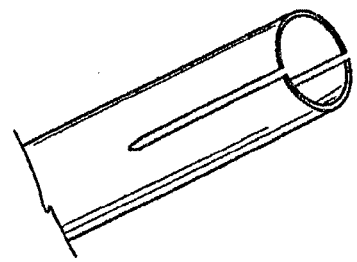
Figure 4W:
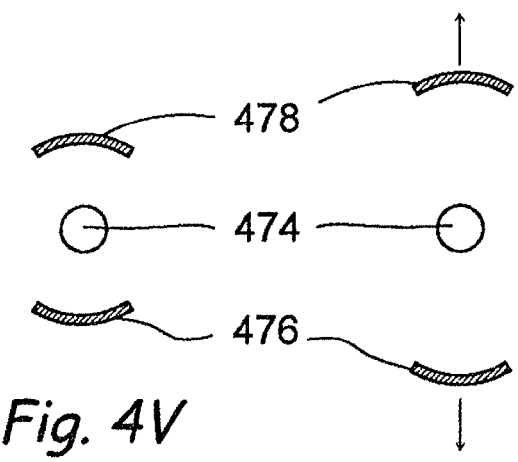
Figure 4W:
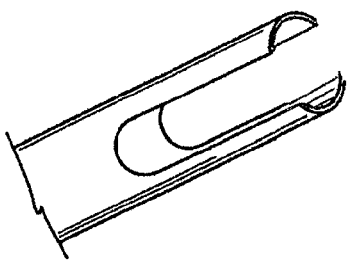

FIGS. 4R through 4W illustrate examples of configurations of mechanical dilators in FIGS. 4H through 4Q. FIG. 4R shows a sectional view of a mechanical dilator comprising an inner member 474, an outer stationary member 476 and an outer bendable member 478. In FIG. 4S, movement of inner member 474 displaces outer bendable member 478 in the radial direction with a force. This force can be used to dilate or displace portions of the anatomy. This configuration is useful to exert force in a particular radial direction. FIG. 4S' shows a partial perspective view of the outer stationary member 476 of FIG. 4R. FIG. 4T shows a sectional view of a mechanical dilator comprising an inner member 480, a first outer hemi-tubular member 482 and a second outer hemi-tubular member 484. In FIG. 4U, movement of inner member 480 displaces first outer hemi-tubular member 482 and second outer hemi-tubular member 484 in the radial direction with a force. This force can be used to dilate or displace portions of the anatomy. This configuration is useful to exert force in two diametrically opposite regions. FIG. 4U' shows a partial perspective view of the first outer hemi-tubular member 482 and the second outer hemi-tubular member 484 of FIG. 4T. FIG. 4V shows a sectional view of a mechanical dilator comprising an inner member 486, a first outer curved member 488 and a second outer curved member 490. In FIG. 4W, movement of inner member 486 displaces first outer curved member 488 and second outer curved member 490 in the radial direction with a force. This force can be used to dilate or displace portions of the anatomy. This configuration is useful to exert force over smaller areas in two diametrically opposite regions. FIG. 4W' shows a partial perspective view of the first outer curved member 488 and the second outer curved member 490 of FIG. 4V. Similar designs for mechanical dilators in FIGS. 4H through 4Q are possible using three or more displaceable members. The inner member in the mechanical dilators disclosed herein may be replaced by a balloon for displacing the outer members to exert an outward radial force.

Several other designs of the working device may also be used including but not limited to cutters, chompers, rotating drills, rotating blades, tapered dilators, punches, dissectors, burs, non-inflating mechanically expandable members, high frequency mechanical vibrators, radiofrequency ablation devices, microwave ablation devices, laser devices (e.g. $CO_2$, Argon, potassium titanyl phosphate, Holmium:YAG and Nd:YAG laser devices), snares, biopsy tools, scopes and devices that introduce diagnostic or therapeutic agents.

Figure 5A:
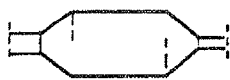
FIG. 5A shows a perspective view of a balloon that comprises a conical proximal portion, a conical distal portion and a cylindrical portion between the conical proximal portion and the conical distal portion.
Figure 5H:
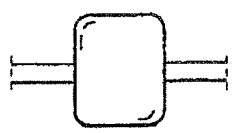
FIG. 5H shows a perspective view of a square balloon.
Figure 5B:
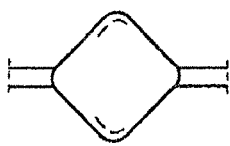
FIG. 5B shows a perspective view of a conical balloon.
Figure 5I:
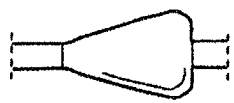
FIG. 5I shows a perspective view of a conical/square balloon.
Figure 5C:
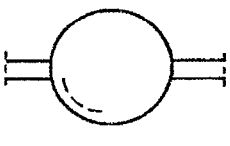
FIG. 5C shows a perspective view of a spherical balloon.
Figure 5J:
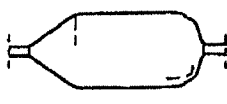
FIG. 5J shows a perspective view of a conical/spherical long balloon.
Figure 5D:
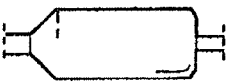
FIG. 5D shows a perspective view of a conical/square long balloon.
Figure 5K:
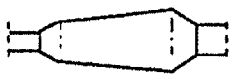
FIG. 5K shows a perspective view of an embodiment of a tapered balloon.
Figure 5E:
FIG. 5E shows a perspective view of a long spherical balloon.
Figure 5L:
FIG. 5L shows a perspective view of a stepped balloon.
Figure 5F:
FIG. 5F shows a perspective view of a bi-lobed "dog bone" balloon.
Figure 5M:
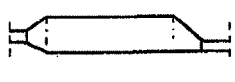
FIG. 5M shows a perspective view of a conical/offset balloon.
Figure 5G:
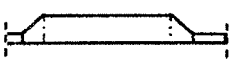
FIG. 5G shows a perspective view of an offset balloon.
Figure 5N:
FIG. 5N shows a perspective view of a curved balloon.
Figure 5:
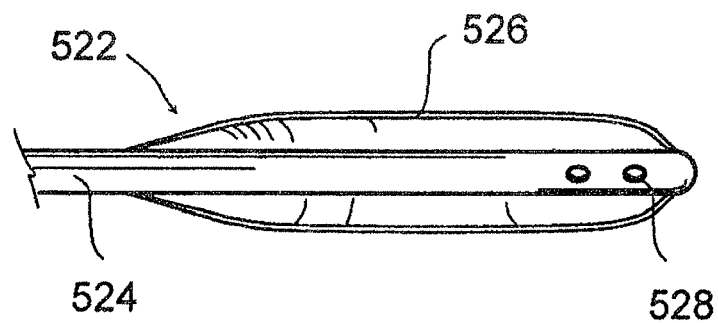
Figure 5:
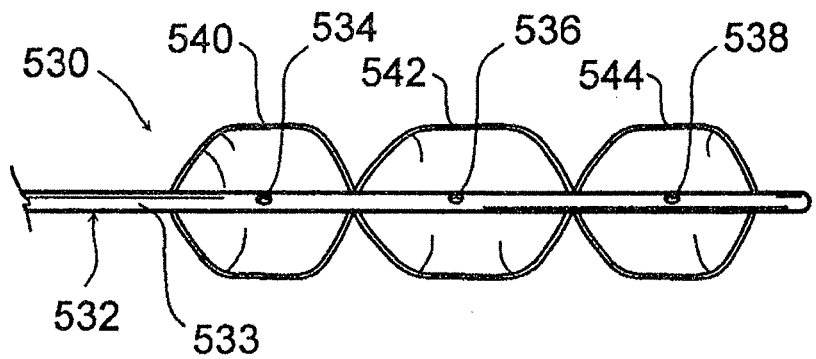
Figure 5:
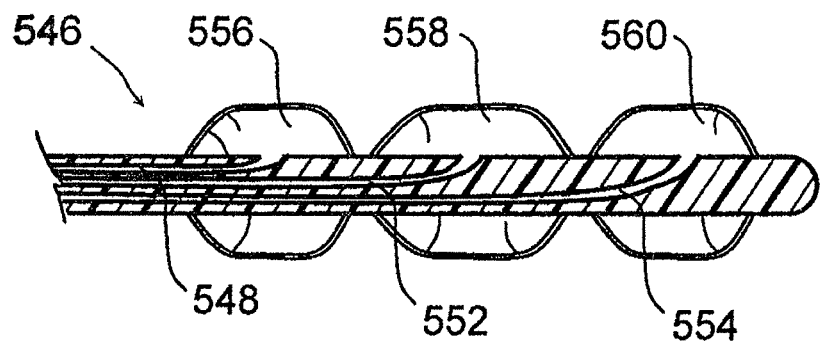
Figure 5:
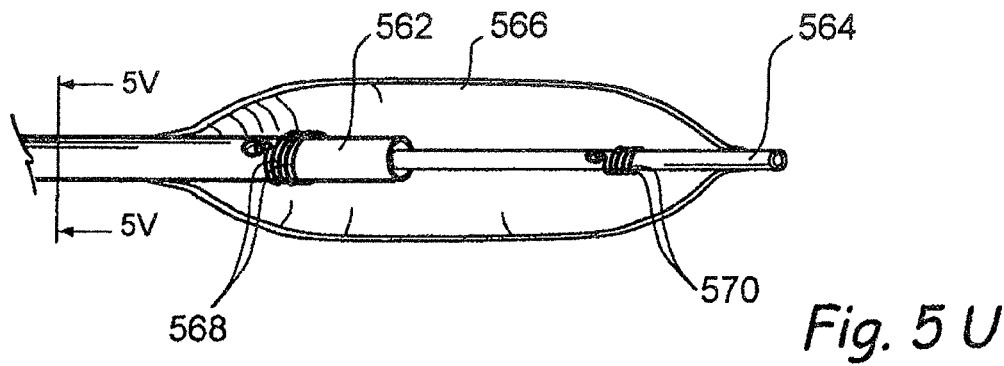
Figure 5:
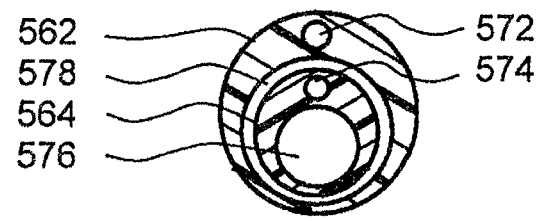
Figure 5:
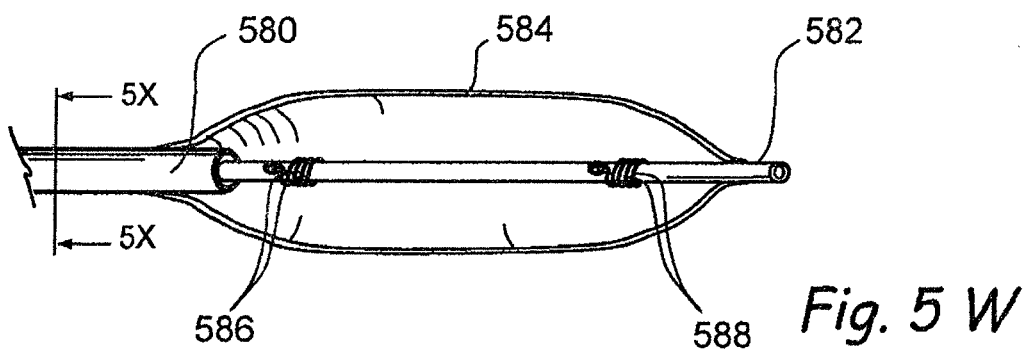
Figure 5:
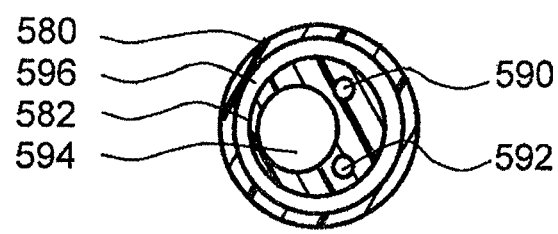

FIG. 5A shows a perspective view of an embodiment of a balloon comprising a conical proximal portion, a conical distal portion and a cylindrical portion between the conical proximal portion and the conical distal portion. FIGS. 5B to 5N show perspective views of several alternate embodiments of the balloon. FIG. 5B shows a conical balloon, FIG. 5C shows a spherical balloon, FIG. 5D shows a conical/square long balloon, FIG. 5E shows a long spherical balloon, FIG. 5F shows a dog bone balloon, FIG. 5G shows a offset balloon, FIG. 5H shows a square balloon, FIG. 5I shows a conical/square balloon, FIG. 5J shows a conical/spherical long balloon, FIG. 5K shows a tapered balloon, FIG. 5L shows a stepped balloon, FIG. 5M shows a conical/offset balloon and FIG. 5N shows a curved balloon.

The balloons disclosed herein can be fabricated from biocompatible materials including but not limited to polyethylene terephthalate, Nylon, polyurethane, polyvinyl chloride, crosslinked polyethylene, polyolefins, HPTFE, HPE, HDPE, LDPE, EPTFE, block copolymers, latex and silicone. The balloons disclosed herein can be fabricated by a variety of fabrication methods including but not limited to molding, blow molding, dipping, extruding etc.

The balloons disclosed herein can be inflated with a variety of inflation media including but not limited to saline, water, air, radiographic contrast materials, diagnostic or therapeutic substances, ultrasound echogenic materials and fluids that conduct heat, cold or electricity.

The balloons in this invention can also be modified to deliver diagnostic or therapeutic substances to the target anatomy. For example, FIG. 5O shows a partial perspective view of an embodiment of a balloon catheter device 500 comprising a balloon for delivering diagnostic or therapeutic substances. Balloon catheter device 500 comprises a flexible catheter 502 having a balloon 504 thereon. The catheter device 500 is advanced, with balloon 504 deflated, into a passageway such as a nostril, nasal cavity, meatus, ostium, interior of a sinus, etc. and positioned with the deflated balloon 504 situated within an ostium, passageway or adjacent to tissue or matter that is to be dilated, expanded or compressed (e.g., to apply pressure for hemostasis, etc.).

Thereafter, the balloon 504 may be inflated to dilate, expand or compress the ostium, passageway, tissue or matter. Thereafter the balloon 504 may be deflated and the device 500 may be removed. This balloon 504 may also be coated, impregnated or otherwise provided with a medicament or substance that will elute from the balloon into the adjacent tissue (e.g., bathing the adjacent tissue with drug or radiating the tissue with thermal or other energy to shrink the tissues in contact with the balloon 504). Alternatively, in some embodiments, the balloon may have a plurality of apertures or openings through which a substance may be delivered, sometimes under pressure, to cause the substance to bathe or diffuse into the tissues adjacent to the balloon. Alternatively, in some embodiments, radioactive seeds, threads, ribbons, gas or liquid, etc. may be advanced into the catheter shaft 502 or balloon 504 or a completely separate catheter body for some period of time to expose the adjacent tissue and to achieve a desired diagnostic or therapeutic effect (e.g. tissue shrinkage, etc.).

The balloons in this invention can have a variety of surface features to enhance the diagnostic or therapeutic effects of a procedure. For example, FIG. 5P shows a partial perspective view of an embodiment of a balloon/cutter catheter device 506 comprising a flexible catheter 508 having a balloon 510 with one or more cutter blades 512 formed thereon. The device 506 is advanced, with balloon 510 deflated, into a passageway such as a nostril, nasal cavity, meatus, ostium, interior of a sinus, etc. and positioned with the deflated balloon 510 situated within an ostium, passageway or adjacent to tissue or matter that is to be dilated, expanded or compressed and in which it is desired to make one or more cuts or scores (e.g. to control the fracturing of tissue during expansion and minimize tissue trauma etc.). Thereafter, the balloon 510 is inflated to dilate, expand or compress the ostium, passageway, tissue or matter and causing the cutter blade(s) 512 to make cut(s) in the adjacent tissue or matter. Thereafter the balloon 510 is deflated and the device 506 is removed. The blade may be energized with mono or bi-polar RF energy or otherwise heated such that it will cut the tissues while also causing hemostasis and/or to cause thermal contraction of collagen fibers or other connective tissue proteins, remodeling or softening of cartilage, etc.

The balloons in this invention can have a variety of reinforcing means to enhance the balloon properties. For example, FIGS. 5Q and 6F show perspective views of an embodiment of a balloon catheter device 514 comprising a flexible catheter 516 having a balloon 518 with one or more reinforcing means 520 thereon. In this example, reinforcing means 520 is a braid attached on the external surface of balloon 518. The reinforcing braid can be constructed from suitable materials like polymer filaments (e.g. PET or Kevlar filaments), metallic filaments (e.g. SS316 or Nitinol filaments) and metallic or non-metallic meshes or sheets. A variety of other reinforcing means can be used including but not limited to reinforcing coatings, external or internal reinforcing coils, reinforcing fabric, reinforcing meshes and reinforcing wires, reinforcing rings, filaments embedded in balloon materials etc. FIG. 6F' shows a perspective view of a reinforcing braid that can be used with the balloon catheter device in FIGS. 5Q and 6F.

The balloons in this invention can have a variety of inflation means to enhance the balloon properties. FIG. 5R shows a partial sectional view of an embodiment of a balloon catheter 522 comprising a shaft 524 and a balloon 526. Shaft 524 comprises a balloon inflation lumen. The distal portion of balloon inflation lumen terminates in inflation ports 528 located near the distal end of balloon 526. Thus, when balloon catheter 522 is inserted in an orifice and balloon 526 is inflated, the distal portion of balloon 526 inflates earlier than the proximal portion of balloon 526. This prevents balloon 526 from slipping back out of the orifice.

FIGS. 5S through 5T illustrate designs of balloon catheters comprising multiple balloons. FIG. 5S shows a partial sectional view of an embodiment of a balloon catheter 530 comprising a shaft 532 with a lumen 533. Lumen 533 opens into three orifices located on shaft 532 namely a first orifice 534, a second orifice 536 and a third orifice 538. The three orifices are used to inflate three balloons. First orifice 534 inflates a first balloon 540, second orifice 536 inflates a second balloon 542 and third orifice 538 inflates third balloon 544. In one embodiment, first balloon 540 and third balloon 544 are inflated with a single lumen and second balloon 542 is inflated with a different lumen. In another embodiment, first balloon 540, second balloon 542 and third balloon 544 interconnected and are inflated with a single lumen. A valve mechanism allows first balloon and second balloon to inflate before allowing second balloon to inflate.

Alternatively, the balloons can be inflated by separate lumens. FIG. 5T shows a partial sectional view of an embodiment of a balloon catheter 546 comprising a shaft 548 comprising a first inflation lumen 550, a second inflation lumen 552 and a third inflation lumen 554. The three inflation lumens are used to inflate three non-connected balloons. First inflation lumen 550 inflates a first balloon 556, second inflation lumen 552 inflates a second balloon 558 and third inflation lumen 554 inflates a third balloon 560.

The devices disclosed herein may comprise one or more navigation or visualization modalities. FIGS. 5U through 5AB illustrate perspective and sectional views of various embodiments of a balloon catheter comprising sensors. FIG. 5U shows a partial perspective view of a balloon catheter comprising an outer member 562, an inner member 564 and a balloon 566 attached to distal region of outer member 562 and distal region of inner member 564. The balloon catheter further comprises a first sensor 568 located on the distal region of outer member 562 and a second sensor 570 located on the distal region of inner member 564. FIG. 5V shows a crossection through plane 5V-5V in FIG. 5U. Outer member 562 comprises a first sensor lumen 572 to receive the lead from first sensor 568. Inner member 564 comprises a second sensor lumen 574 to receive the lead from second sensor 570. Inner member 564 further comprises a circular lumen 576. Outer member 562 and inner member 564 enclose an annular lumen 578. In one embodiment, annular lumen 578 is a balloon inflation lumen.

FIG. 5W shows a partial perspective view of a balloon catheter comprising an outer member 580, an inner member 582 and a balloon 584 attached to distal region of outer member 580 and distal region of inner member 582. The balloon catheter further comprises a first sensor 586 located on the distal region of inner member 582 and a second sensor 588 located on the distal region of inner member 582 distal to first sensor 586. FIG. 5X shows a cross section through plane 5X-5X in FIG. 5W. Inner member 582 comprises a first sensor lumen 590 to receive the lead from first sensor 586 and a second sensor lumen 592 to receive the lead from second sensor 588. Inner member 582 further comprises a circular lumen 594. Outer member 580 and inner member 582 enclose an annular lumen 596. In one embodiment, annular lumen 596 is a balloon inflation lumen.

Figure 5Y:
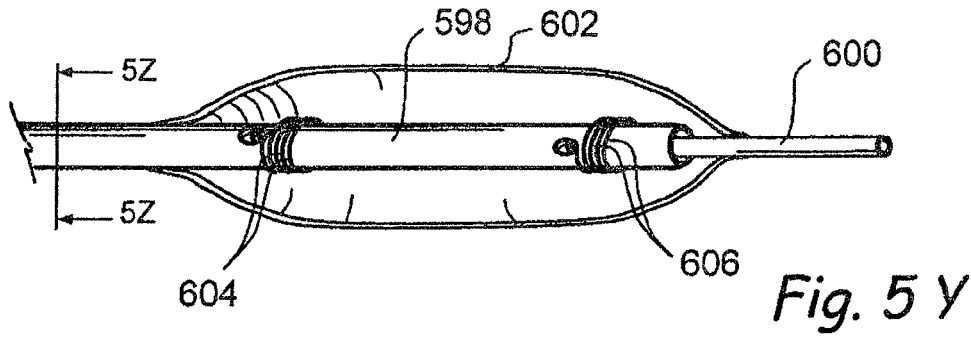
Figure 5Z:
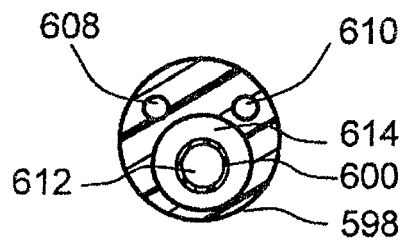
Figure 5A:
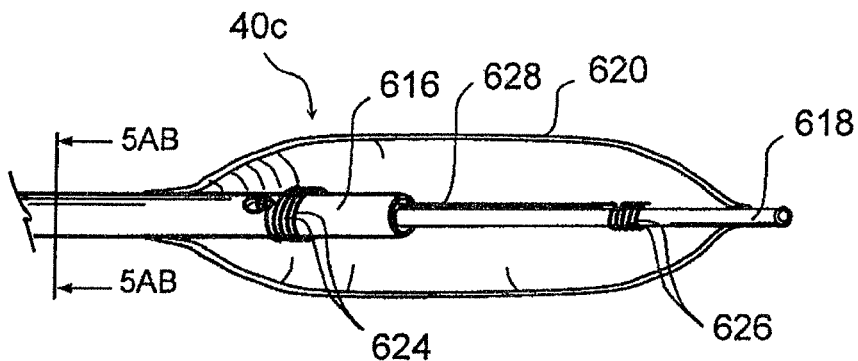
Figure 5A:
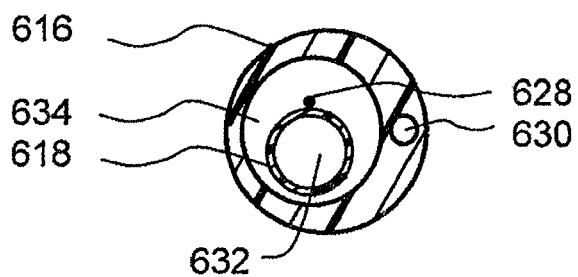

FIG. 5Y shows a partial perspective view of a balloon catheter comprising an outer member 598, an inner member 600 and a balloon 602 attached to distal region of outer member 598 and distal region of inner member 600. The balloon catheter further comprises a first sensor 604 located on the distal region of outer member 598 and a second sensor 606 located on the distal region of outer member 598 distal to first sensor 604. FIG. 5Z shows a cross section through plane 5Z-5Z in FIG. 5Y. Outer member 598 comprises a first sensor lumen 608 to receive the lead from first sensor 604 and a second sensor lumen 610 to receive the lead from second sensor 606. Inner member 600 comprises a circular lumen 612. Outer member 598 and inner member 600 enclose an annular lumen 614. In one embodiment, annular lumen 614 is a balloon inflation lumen.

The leads from the sensors may be attached on the surface of an element of the balloon catheter without being enclosed in a lumen. FIG. 5AA shows a partial perspective view of a balloon catheter comprising an outer member 616, an inner member 618 and a balloon 620 attached to distal region of outer member 616 and distal region of inner member 618. The balloon catheter further comprises a first sensor 624 located on the distal region of outer member 616 and a second sensor 626 located on the distal region of inner member 618. Second sensor 626 comprises a lead 628. FIG. 5AB shows a cross section through plane 5AB-5AB in FIG. 5AA. Outer member 616 comprises a first sensor lumen 630 to receive the lead from first sensor 624. Inner member 618 comprises a circular lumen 632. Lead 628 from second sensor 626 is attached on the outer surface of inner member 618 and is oriented parallel to inner member 618. Outer member 616 and inner member 618 enclose an annular lumen 634. In one embodiment, annular lumen 634 is a balloon inflation lumen. The sensors mentioned in FIGS. 5U through 5AB can be electromagnetic sensors or sensors including but not limited to location sensors, magnetic sensors, electromagnetic coils, RF transmitters, mini-transponders, ultrasound sensitive or emitting crystals, wire-matrices, micro-silicon chips, fiber-optic sensors, etc.

Figure 6A:
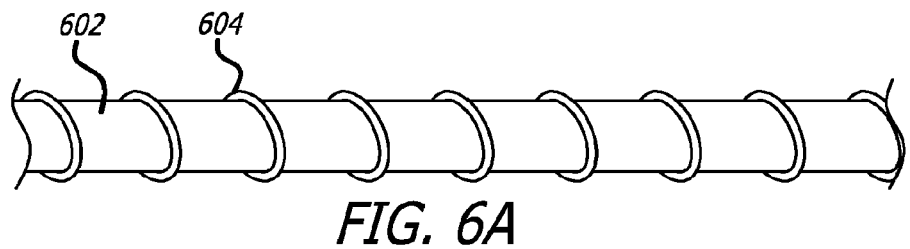
FIG. 6A shows a partial perspective view of a shaft design useable in the various devices disclosed herein, wherein the shaft comprises an external spiral wire.
Figure 6B:
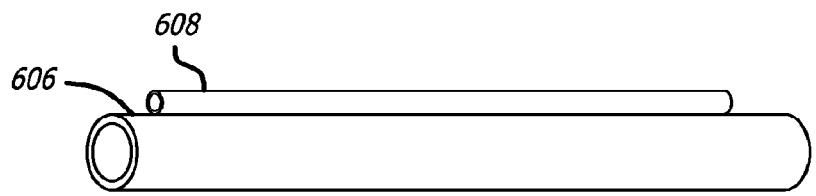
FIG. 6B shows a partial perspective view of a shaft design for the various devices disclosed herein, wherein the shaft comprises a stiffening wire.
Figure 6C:
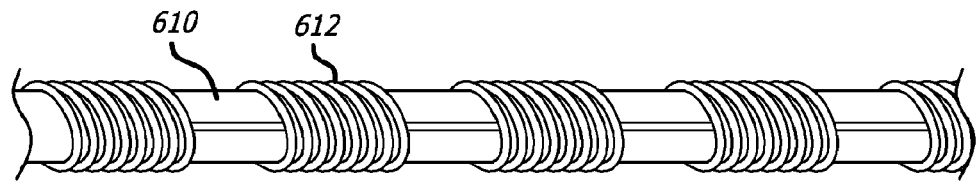
FIG. 6C shows a partial perspective view of an embodiment of a shaft design for the various devices disclosed herein, wherein the shaft comprises stiffening rings.
Figure 6D:
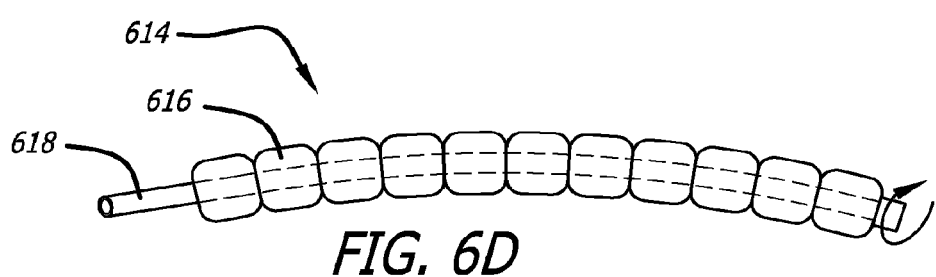
FIG. 6D shows a partial perspective view of a shaft design for the various devices disclosed herein, wherein the shaft comprises controllable stiffening elements.
Figure 6E:
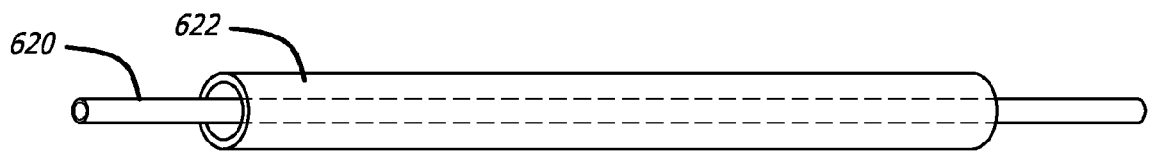
FIG. 6E shows a partial perspective view of a shaft design for the various devices disclosed herein, wherein the shaft comprises a hypotube.
Figure 6:
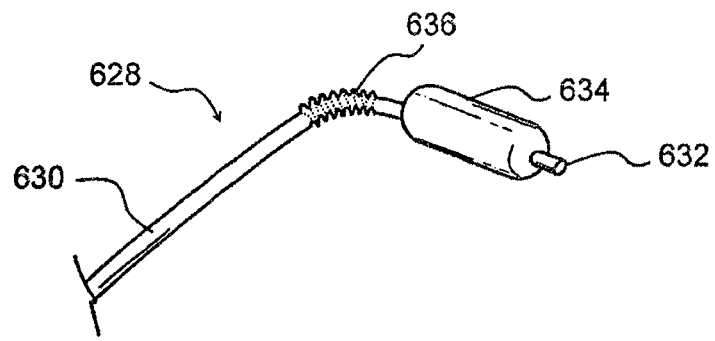
FIG. 6F shows a partial perspective cut-away view of a shaft design for the various devices disclosed herein, wherein the shaft comprises a braid.
FIG. 6G shows a partial perspective view of an embodiment of a device comprising a shaft having a plastically deformable region.
FIG. 6H shows a partial perspective view of a device comprising a shaft having a flexible element.
FIG. 6I shows a partial perspective view of a shaft comprising a malleable element.
FIG. 6J shows a partial perspective view of the shaft of FIG. 6I in a bent configuration.
FIG. 6K shows a cross sectional view through plane 6K-6K of FIG. 6I.
FIG. 6L shows a partial sectional view of an embodiment of a controllably deformable shaft.
FIG. 6M shows a partial sectional view of the controllably deformable shaft of FIG. 6L in a deformed state.
FIG. 6N shows a perspective view of a balloon catheter comprising a rigid or semi-rigid member.
FIGS. 6O through 6Q show sectional views of a balloon catheter that comprises an insertable and removable element.
Figure 6:
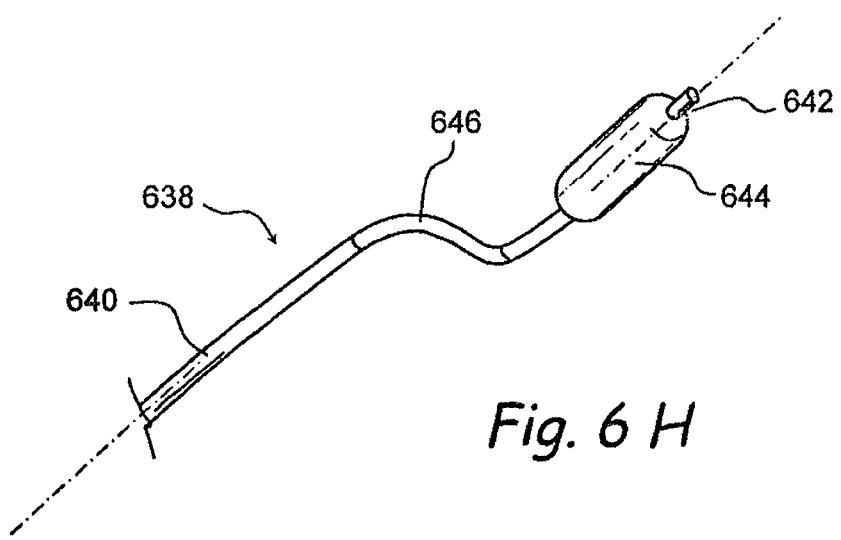
Figure 6:
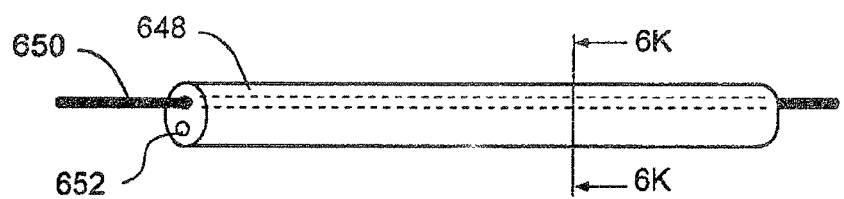
Figure 6:
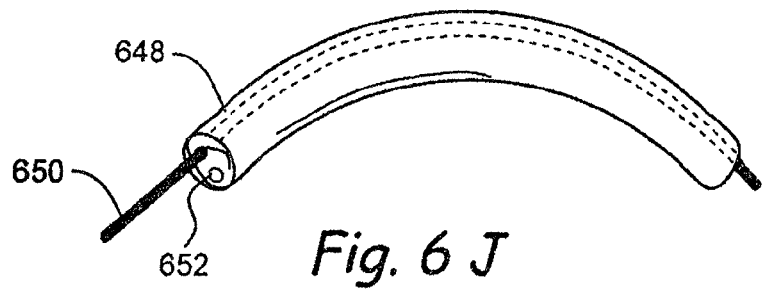
Figure 6:
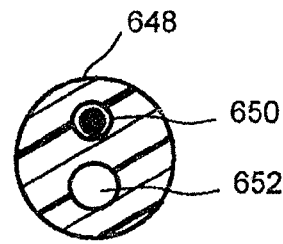
Figure 6:
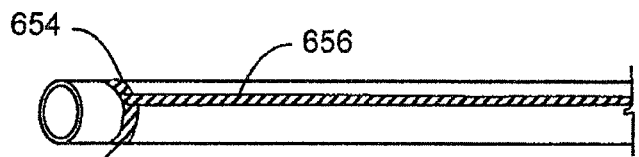
Figure 6:
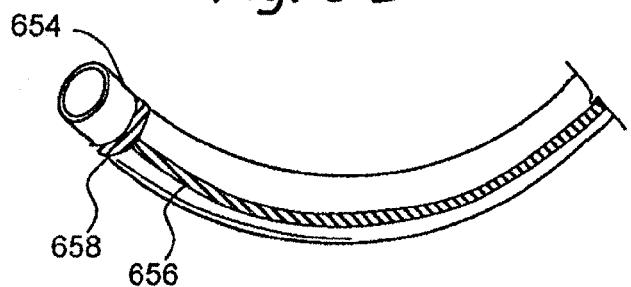
Figure 6:
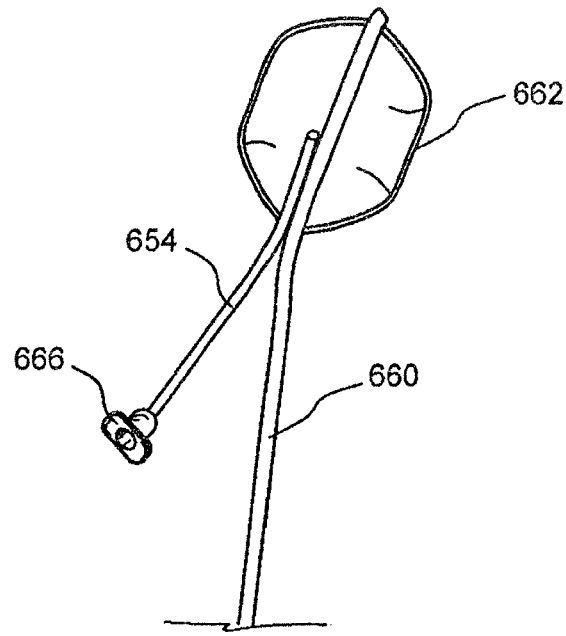
Figure 6:
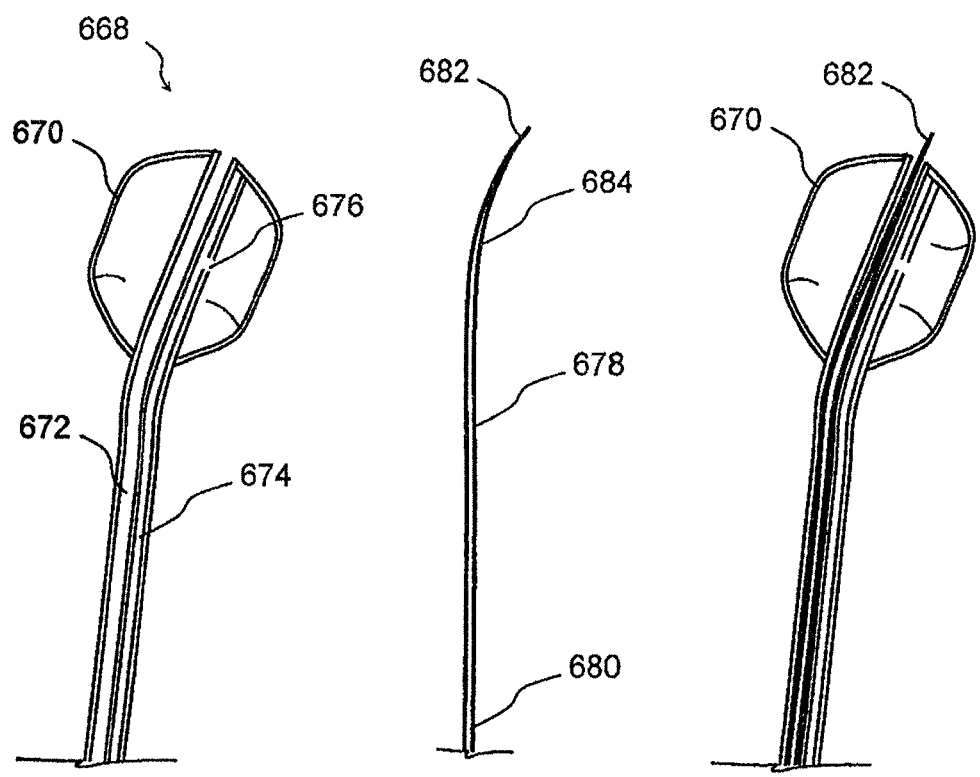

FIGS. 6A through 6G illustrate partial perspective views of several embodiments of shaft designs for the various devices disclosed herein. These shaft designs are especially useful for devices that encounter high torque or high burst pressures or require enhanced pushability, steerability and kink resistance. FIG. 6A shows a partial perspective view of an embodiment of a shaft 602 comprising a spiral element 604 wound around the shaft. Spiral element 604 can be made of suitable materials like metals (e.g. SS316L, SS304) and polymers. In one embodiment, spiral element 604 is in the form of round wire of diameter between 0.04 mm to 0.25 mm. In another embodiment, spiral element is in the form of flat wire of cross section dimensions ranging from 0.03 mm×0.08 mm to 0.08 mm×0.25 mm. FIG. 6B shows a partial perspective view of an embodiment of a shaft 606 comprising a reinforcing filament 608. Reinforcing filament 608 is substantially parallel to the axis of shaft 606. Shaft 606 with reinforcing filament 608 can be covered with a jacketing layer. Reinforcing filament 608 can be made of suitable materials like metals, polymers, glass fiber etc. Reinforcing filament 608 can also have shape memory characteristics. In one embodiment, reinforcing filament 608 is embedded in shaft 606. In another embodiment, reinforcing filament is introduced through a lumen in shaft 606. Shaft 606 may comprise more than one reinforcing filament 608. FIG. 6C shows a partial perspective view of an embodiment of a shaft 610 comprising one of more stiffening rings 612 along the length of shaft 610. FIG. 6D shows a partial perspective view of an embodiment of a shaft 614 comprising a series of controllably stiffening elements 616 along the length of the shaft. Shaft 614 further comprises a tension wire 618 that runs through controllably stiffening elements 616 and is attached to the most distal stiffening element. The tension in tension wire 618 causes controllably stiffening elements 616 to come into contact with each other with a force. Friction between controllably stiffening elements 616 causes shaft 614 to have a certain stiffness. Increasing the tension in tension wire 618 increases the force with which controllably stiffening elements 616 come into contact with each other. This increases the friction between controllably stiffening elements 616 which in turn increases the stiffness of shaft 614. Similarly, reducing the tension in tension wire 618 reduces the stiffness of shaft 614. Controllably stiffening elements 616 can be made from suitable materials like metal, polymers and composites. In one embodiment, controllably stiffening elements 616 are separated from each other by one or more springs. Tension wire 618 can be made from metals like SS316. Tension wire 618 may also be used to cause the device to actively bend or shorten in response to tension. FIG. 6E shows a partial perspective view of an embodiment of a shaft 620 comprising a hypotube 622. In one embodiment, hypotube 622 is located on the exterior surface of shaft 620. In another embodiment, hypotube 622 is embedded in shaft 620. Hypotube 620 can be made of metals like stainless steel 316 or suitable polymers. FIGS. 6F and 6F' show a partial perspective view of an embodiment of a shaft 624 comprising a reinforcing element 626 in the form of a reinforcing braid or mesh located on the outer surface of shaft 624. Reinforcing element 626 can be made of suitable materials like polymer filaments (e.g. PET or Kevlar filaments), metallic wires e.g. SS316 wires etc. The braid pattern can be regular braid pattern, diamond braid pattern, diamond braid pattern with a half load etc. In one embodiment, the outer surface of reinforcing element 626 is covered with a jacketing layer.

The shafts of various devices disclosed herein may be non homogenous along their length. Examples of such shafts are illustrated in FIGS. 6G through 6H. FIG. 6G shows a partial perspective view of an embodiment of a device comprising a shaft 628 comprising a proximal portion 630, a distal portion 632, a working element 634 and a plastically deformable region 636 located between the proximal portion 630 and distal portion 632. Plastically deformable region 636 can be deformed by a physician to adjust the angle between proximal portion 630 and distal portion 632. This enables the devices to be used for several different anatomical regions of the same patient. Also, such devices can be adjusted for optimal navigation through a patient's anatomy. In one embodiment, shaft 628 comprises multiple plastically deformable regions. In another embodiment plastically deformable region 636 is located within working element 634. Such a design comprising one or more plastically deformable regions can be used for any of the devices mentioned herein like catheters with working elements, guide catheters, guide catheters with a pre-set shape, steerable guide catheters, steerable catheters, guidewires, guidewires with a pre-set shape, steerable guidewires, ports, introducers, sheaths etc.

FIG. 6H shows a partial perspective view of an embodiment of a device comprising a shaft with a flexible element. The design is illustrated as a shaft 638 comprising a proximal portion 640, a distal portion 642 and a working element 644 (e.g. a balloon). Shaft 638 further comprises a flexible element 646 located between proximal portion 640 and distal portion 642. This design enables proximal portion 640 to bend with respect to distal portion 642 making it easier to navigate through the complex anatomy and deliver working element 644 to the desired location. In one embodiment, shaft 638 comprises multiple flexible elements. In another embodiment, flexible element 646 is located within working element 644. Such a design comprising one or more flexible elements can be used for any of the devices mentioned herein like catheters with working elements, guide catheters, guide catheters with a pre-set shape, steerable guide catheters, steerable catheters, guidewires, guidewires with a pre-set shape, steerable guidewires, ports, introducers, sheaths etc.

FIGS. 6I through 6K illustrate an example of a shaft comprising a malleable element. FIG. 6I shows a partial perspective view of an embodiment of a shaft 648 comprising malleable element 650 and a lumen 652 wherein shaft 648 is in a substantially straight configuration. Malleable element 650 is embedded in shaft 648 such that the axis of malleable element 650 is substantially parallel to the axis of shaft 648. FIG. 6J shows a partial perspective view of the embodiment of FIG. 6I in a bent configuration. FIG. 6K shows a cross sectional view through plane 6K-6K of FIG. 6I showing shaft 648 comprising malleable element 650 and a lumen 652. In one embodiment, shaft 648 comprises more than one malleable element.

FIGS. 6L through 6M show an embodiment of a controllably deformable shaft. FIG. 6L shows a partial sectional view of an embodiment of a controllably deformable shaft 654 comprising a pull wire 656 attached to a pull wire terminator 658 located near the distal end of shaft 654. FIG. 6M shows a partial sectional view of the controllably deformable shaft 654 of FIG. 6L in a bent orientation when pull wire 656 is pulled in the proximal direction. The deformation can be varied by varying the location of pull wire terminator 658 and the stiffness of various sections of shaft 658. The stiffness of a section of shaft 658 can be varied by adding reinforcing coatings, external or internal reinforcing coils, reinforcing fabric, reinforcing meshes and reinforcing wires, hinged elements, embedded filaments, reinforcing rings etc.

FIG. 6N shows a perspective view of a balloon catheter comprising a rigid or semirigid member. The balloon catheter comprises a rigid or semi-rigid member 660 and a balloon 662 located on the distal region of rigid or semi-rigid member 660. Rigid or semi-rigid member 660 may comprise one or more lumens. Rigid or semi-rigid member 660 may comprise one or more bent, curved or angled regions. Balloon 662 is inflated by a balloon inflation tube 664 comprising a hub 666 at the proximal end of balloon inflation tube 664. In one embodiment, balloon inflation tube 664 is fully attached along its length to rigid or semi-rigid member 660. In another embodiment, balloon inflation tube 664 is partially attached along its length to rigid or semi-rigid member 660.

FIGS. 6O through 6Q illustrate sectional views of a balloon catheter comprising an insertable and removable element. FIG. 6O shows a balloon catheter 668 comprising a balloon 670, a first lumen 672 and a balloon inflation lumen 674 opening into balloon 670 through an inflation port 676. FIG. 6P shows an insertable element 678 having a proximal end 680 and a distal end 682. In one embodiment, distal end 682 ends in a sharp tip for penetrating tissue. In one embodiment, insertable element 678 comprises one or more bent, angled or curved regions 684. Insertable element 678 can be fabricated from a variety of materials to obtain properties including but not limited to rigidity, shape memory, elasticity, ability to be plastically deformed etc. In FIG. 6Q, insertable element 678 is inserted into balloon catheter 668 through first lumen 672. This combination can be used to perform a diagnostic or therapeutic procedure. Insertable element 678 may be removed during or after the procedure.

Figure 7A:
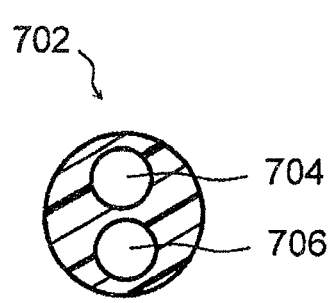
FIG. 7A shows a cross sectional view through a balloon catheter shaft comprising two cylindrical lumens.
Figure 7B:
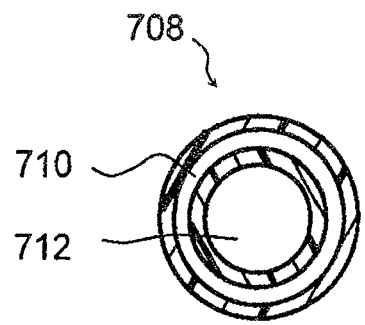
FIG. 7B shows a cross sectional view through a balloon catheter shaft comprising an inner lumen and an annular outer lumen disposed about the inner lumen.
Figure 7C:
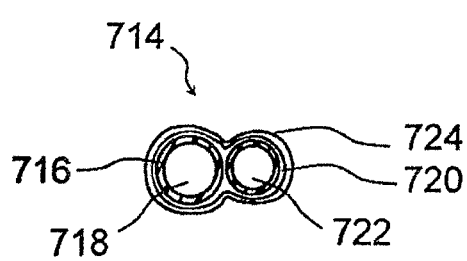
FIG. 7C shows a cross sectional view through a balloon catheter shaft which comprises a first tubular element with a first lumen, a second tubular element with a second lumen and a jacket surrounding the first and second tubular elements.
Figure 7D:
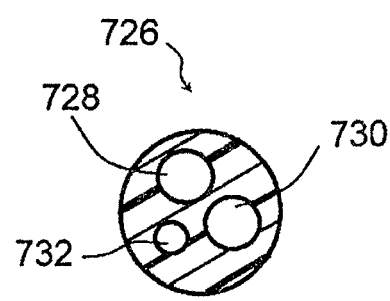
FIG. 7D shows a cross sectional view through a balloon catheter shaft comprising three lumens.
Figure 7E:
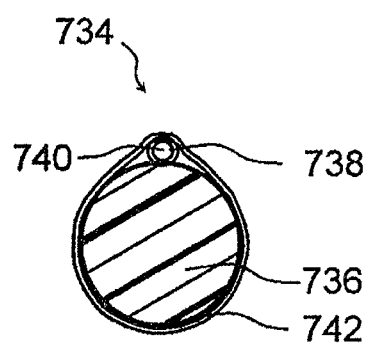
FIG. 7E shows a cross sectional view through a balloon catheter shaft comprising a cylindrical element, a tubular element that has a lumen and a jacket surrounding the cylindrical element and the tubular element.
Figure 7F:
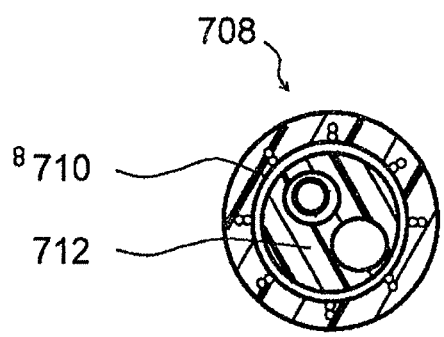
FIG. 7F shows a cross sectional view through a balloon catheter shaft comprising an embedded braid.
Figure 7:
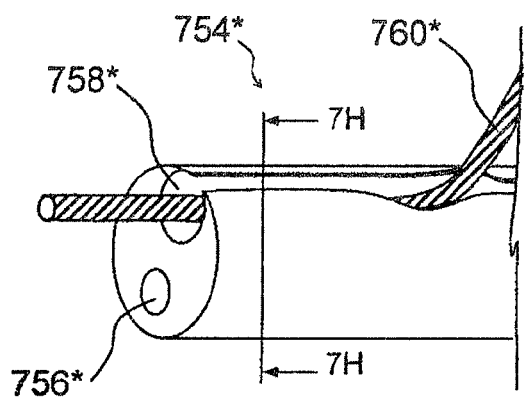
FIG. 7G shows a partial perspective view of a catheter shaft comprising a zipper lumen with a guide extending through a portion of the zipper lumen.
FIG. 7H shows a cross sectional view through line 7H-7H of FIG. 7G.
FIG. 7I shows a partial longitudinal sectional view of a catheter shaft comprising a rapid exchange lumen with a guide extending through the rapid exchange lumen.
FIG. 7J shows a cross sectional view of the catheter shaft of FIG. 7I through line 7J-7J.
FIG. 7K shows a cross sectional view of the catheter shaft of FIG. 7I through line 7K-7K.
FIG. 7L is a partial perspective view of a balloon catheter device of the present invention comprising a through lumen and a balloon inflation lumen within the shaft of the catheter.
FIG. 7M is a cross sectional view through line 7M-7M of FIG. 7L.
FIG. 7N is a cross sectional view through line 7N-7N of FIG. 7L.
FIG. 7O is a partial perspective view of another balloon catheter device of the present invention comprising a through lumen within the shaft of the catheter and a balloon inflation tube disposed next to and optionally attached to the catheter shaft.
FIG. 7P is a cross sectional view through line 7P-7P of FIG. 7O.
FIG. 7Q is a cross sectional view through line 7O-7O of FIG. 7.
Figure 7:
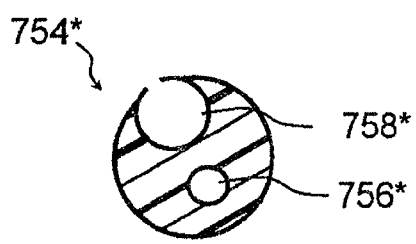
Figure 7:
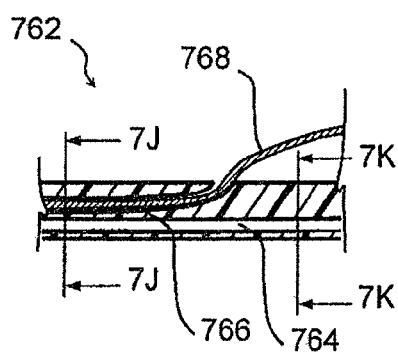
Figure 7:
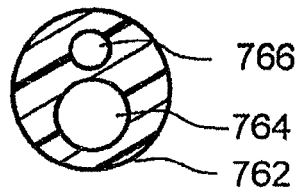
Figure 7:
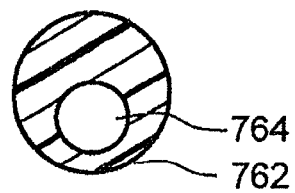

FIGS. 7A through 7K show cross sectional views of several embodiments of lumen orientation in the devices disclosed herein. FIG. 7A shows a cross sectional view of an embodiment of a shaft 702 comprising a first lumen 704 and a second lumen 706. In one embodiment, first lumen 704 is a guidewire lumen and second lumen 706 is an inflation lumen. FIG. 7B shows a cross sectional view of an embodiment of a shaft 708 comprising a first lumen 710 and a annular second lumen 712 such that second annular lumen 712 is substantially coaxial with first lumen 710. In one embodiment, first lumen 710 is a guidewire lumen and annular second lumen 712 is an inflation lumen. FIG. 7C shows a cross sectional view of an embodiment of a shaft 714 comprising a first tubular element 716 comprising a first lumen 718, a second tubular element 720 comprising a second lumen 722 and a jacket 724 surrounding first tubular element 716 and second tubular element 720. In one embodiment, first lumen 718 is a guidewire lumen and second lumen 722 is an inflation lumen. FIG. 7D shows a cross sectional view of an embodiment of a shaft 726 comprising a first lumen 728, a second lumen 730 and a third lumen 732. In one embodiment, first lumen 728 is a guidewire lumen, second lumen 730 is an irrigation/aspiration lumen and third lumen 732 is an inflation lumen. FIG. 7E shows a cross sectional view of an embodiment of a shaft 734 comprising a cylindrical element 736, a tubular element 738 comprising a lumen 740 and a jacket 742 surrounding cylindrical element 736 and tubular element 738. FIG. 7F shows a cross sectional view of an embodiment of a shaft 744 comprising a tubular member 746 comprising a first lumen 748 and a second lumen 750; a first coating 752 located on the outer surface of tubular member 746; a braid 754 located on the outer surface of first coating 752 and a second coating 756 surrounding braid 754. First lumen 748 is lined with a suitable coating 758 like hydrophilic lubricious coating, hydrophobic lubricious coating, abrasion resisting coating etc. In one embodiment, first lumen 748 is a guidewire lumen and second lumen 750 is an inflation lumen. The lumens disclosed herein can be lined with suitable coatings like hydrophilic lubricious coatings, hydrophobic lubricious coatings, abrasion resisting coatings, radiopaque coatings, echogenic coatings etc.

FIG. 7G shows a partial perspective view of an embodiment of a shaft 754* comprising a first lumen 756* and a zipper lumen 758*. Zipper lumen 758* allows a device like a guidewire 760* to be easily introduced into or removed from shaft 754*. FIG. 7H shows a cross sectional view through plane 7H-7H in FIG. 7G showing the orientations of first lumen 756* and zipper lumen 758*.

FIG. 7I shows a cross sectional view of an embodiment of a shaft 762 comprising a first lumen 764 and a rapid exchange lumen 766. Rapid exchange lumen 766 extends from the distal end of shaft 762 to a proximal region. Rapid exchange lumen 766 enables shaft 762 to be easily and quickly introduced or removed over an exchange device like a guidewire 768. FIG. 7J shows a cross sectional view through plane 7J-7J in FIG. 7I showing first lumen 764 and rapid exchange lumen 766. FIG. 7K shows a cross sectional view through plane 7K-7K in FIG. 7I showing first lumen 764.

Figure 7L:
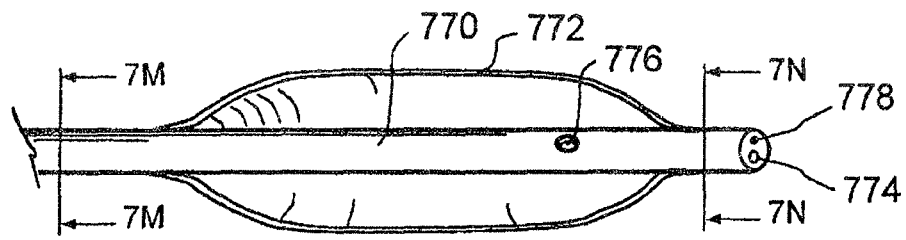
Figure 7M:
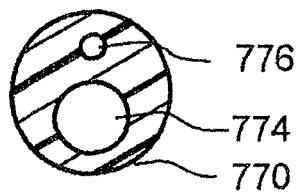
Figure 7N:
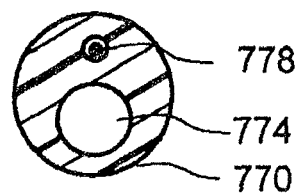
Figure 7O:
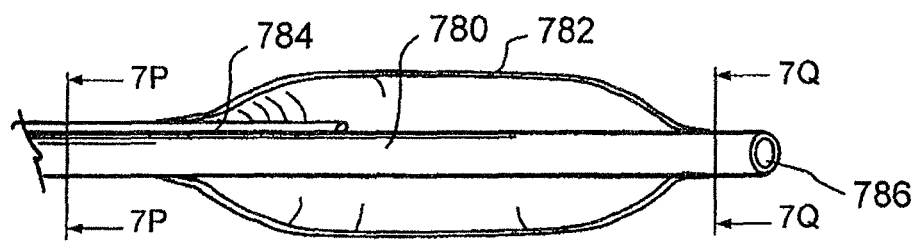
Figure 7P:
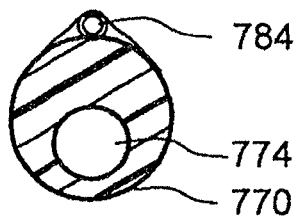
Figure 7Q:
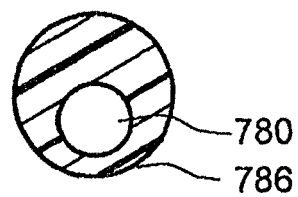

FIGS. 7L through 7Q shows perspective and sectional views of lumens for the devices disclosed herein that are not present throughout the length of the devices. FIG. 7L shows a perspective view of a balloon catheter comprising a shaft 770, a balloon 772 and a lumen 774 that is present throughout shaft 770. The balloon catheter further comprises a balloon inflation lumen 776 that opens into balloon 772. The distal end of balloon inflation lumen 776 is plugged with a plug 778. FIG. 7M shows a crossection through plane 7M-7M in FIG. 7L showing shaft 770 comprising lumen 774 and balloon inflation lumen 776. FIG. 7N shows a crossection through plane 7N-7N in FIG. 7L showing shaft 770 comprising lumen 774 and plug 778. FIG. 7O shows a perspective view of a balloon catheter comprising a shaft 780, a balloon 782 and a lumen 786 that is present throughout shaft 780. The balloon catheter further comprises a balloon inflation lumen 784. The distal end of balloon inflation lumen 784 opens into balloon 782. FIG. 7P shows a crossection through plane 7P-7P in FIG. 7O showing shaft 780 comprising lumen 786 and balloon inflation lumen 784. FIG. 7Q shows a crossection through plane 7Q-7Q in FIG. 7O showing shaft 780 comprising lumen 786.

FIGS. 8A through 8E show partial perspective views of several embodiments of markers that may be present on the elements of the devices mentioned herein. FIG. 8A shows a partial perspective view of an embodiment of a shaft 800 comprising a plurality of distance markers 802 located along the length of shaft 800. FIG. 8B shows a partial perspective view of an embodiment of a shaft 804 comprising a plurality of radiographic markers 806 located along the length of shaft 804. FIG. 8C shows a partial perspective view of an embodiment of a shaft 808 comprising a plurality of ring shaped radiographic markers 810 located along the length of shaft 808. FIG. 8D shows a partial perspective view of an embodiment of a balloon catheter 812 comprising a shaft 814 and a balloon 816. Balloon 816 comprises a plurality of radiographic markers 818 located on the outer surface of the balloon 816. Such markers 818 may be in a linear arrangement, non-linear arrangement or any other configuration that performs the desired marking function (e.g., delineating the length and/or diameter of the balloon, marking the proximal and/or distal ends of the balloon, etc.). FIGS. 8E and 8E' show partial perspective and longitudinal sectional views of an embodiment of a balloon catheter 820 comprising a shaft 822 and a balloon 824. Balloon 824 comprises a plurality of radiographic markers 826 located on the inner surface of the balloon 824. Such markers 826 may be in a linear arrangement, non-linear arrangement or any other configuration that performs the desired marking function (e.g., delineating the length and/or diameter of the balloon, marking the proximal and/or distal ends of the balloon, etc.). The devices disclosed herein may also comprise several other types of markers like ultrasound markers, radiofrequency markers and magnetic markers. Similarly, the devices disclosed herein may also comprise one or more sensors like electromagnetic sensors, electrical sensors, magnetic sensors, light sensors and ultrasound sensors.

The term "diagnostic or therapeutic substance" as used herein is to be broadly construed to include any feasible drugs, prodrugs, proteins, gene therapy preparations, cells, diagnostic agents, contrast or imaging agents, biologicals, etc. Such substances may be in bound or free form, liquid or solid, colloid or other suspension, solution or may be in the form of a gas or other fluid or nan-fluid. For example, in some applications where it is desired to treat or prevent a microbial infection, the substance delivered may comprise pharmaceutically acceptable salt or dosage form of an antimicrobial agent (e.g., antibiotic, antiviral, antiparasitic, antifungal, etc.), a corticosteroid or other anti-inflammatory (e.g., an NSAID), a decongestant (e.g., vasoconstrictor), a mucous thinning agent (e.g., an expectorant or mucolytic), an agent that prevents of modifies an allergic response (e.g., an antihistamine, cytokine inhibitor, leucotriene inhibitor, IgE inhibitor, immunomodulator), etc. Other non-limiting examples of diagnostic or therapeutic substances that may be useable in this invention are described in copending U.S. patent application Ser. No. 10/912,578 entitled Implantable Devices and Methods for Delivering Drugs and Other Substances to Treat Sinusitis and Other Disorders filed on Aug. 4, 2004, issued as U.S. Pat. No. 7,361,168 on Apr. 22, 2008, the entire disclosure of which is expressly incorporated herein by reference.

The term "nasal cavity" used herein to be broadly construed to include any cavity that is present in the anatomical structures of the nasal region including the nostrils and paranasal sinuses.

The term "trans-nasal" means through a nostril.

Although the methods and devices disclosed herein are illustrated in conjunction with particular paranasal sinuses, it is understood that these methods and devices can be used in other paranasal sinuses as well as other anatomical passageways of the ear, nose or throat.

Optionally, any of the working devices and guide catheters described herein may be configured or equipped to receive or be advanced over a guidewire or other guide member (e.g., an elongate probe, strand of suture material, other elongate member) unless to do so would render the device inoperable for its intended purpose. Some of the specific examples described herein include guidewires, but it is to be appreciated that the use of guidewires and the incorporation of guidewire lumens is not limited to only the specific examples in which guidewires or guidewire lumens are shown. The guidewires used in this invention may be constructed and coated as is common in the art of cardiology. This may include the use of coils, tapered or non-tapered core wires, radioopaque tips and/or entire lengths, shaping ribbons, variations of stiffness, PTFE, silicone, hydrophilic coatings, polymer coatings, etc. For the scope of this invention, these wires may possess dimensions of length between 5 and 75 cm and outer diameter between 0.005" and 0.050".

Several modalities can be used with the devices and methods disclosed herein for navigation and imaging of the devices within the anatomy. For example, the devices disclosed herein may comprise an endoscope for visualization of the target anatomy. The devices may also comprise ultrasound imaging modalities to image the anatomical passageways and other anatomical structures. The devices disclosed herein may comprise one or more magnetic elements especially on the distal end of the devices. Such magnetic elements may be used to navigate through the anatomy by using external magnetic fields. Such navigation may be controlled digitally using a computer interface. The devices disclosed herein may also comprise one or more markers (e.g. infra-red markers). The markers can be used to track the precise position and orientation of the devices using image guidance techniques. Several other imaging or navigating modalities including but not limited to fluoroscopic, radiofrequency localization, electromagnetic, magnetic and other radiative energy based modalities may also be used with the methods and devices disclosed herein. These imaging and navigation technologies may also be referenced by computer directly or indirectly to pre-existing or simultaneously created 3-D or 2D data sets which help the doctor place the devices within the appropriate region of the anatomy.

The distal tip of devices mentioned herein may comprise a flexible tip or a soft, atraumatic tip. Also, the shaft of such devices may be designed for enhanced torquability.

The embodiments herein have been described primarily in conjunction with minimally invasive procedures, but they can also be used advantageously with existing open surgery or laparoscopic surgery techniques.

It is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unsuitable for its intended use. All reasonable additions, deletions, modifications and alterations are to be considered equivalents of the described examples and embodiments and are to be included within the scope of the following claims.

What is claimed is:

1. A device for treating a patient, the device comprising:
   (a) an elongate shaft comprising an open proximal end, an open distal end including a tip, an exterior surface, and an outer diameter sized to allow the shaft to be inserted into a patient's nose, wherein at least a portion of the shaft extends along an axis;
   (b) a treatment member coupled with the shaft at or near the tip, wherein the shaft includes a flexible portion, wherein at least a portion of the flexible portion is coincident with the treatment member such that at least a portion of the tip is deflectable between a first position where the tip is oriented at a first angle relative to the axis, and a second position where the tip is oriented at a second angle relative to the axis;
   (c) a steering wire coupled with the treatment member such that a portion of the steering wire can be retracted into the treatment member and advanced from the treatment member;
   (d) a handle extending from the proximal end of the elongate shaft; and
   (e) a control element movably coupled with the handle and the steering wire, wherein the control element is movable in a first direction to thereby retract the portion of the steering wire, wherein the control element is movable in a second direction to thereby advance the portion of the steering wire.

2. The device of claim 1, wherein the treatment member is selected from the group consisting of balloon catheters, rotating cutters, high frequency mechanical vibrators, rotating drills, sequential dilators, tapered dilators, punches, electrocautery devices, cutters, mechanically expandable members, dilating stents and devices that introduce diagnostic or therapeutic agents.

3. The device of claim 1, wherein the first angle is approximately zero degrees.

4. The device of claim 1, wherein the elongate shaft further comprises a guidewire lumen.

5. The device of claim 1, further comprising at least one shaft stiffening member removably coupled with the shaft for stiffening the flexible portion.

6. The device of claim 5, wherein the at least one shaft stiffening member comprises an external stiffening element.

7. The device of claim 5, wherein the at least one shaft stiffening member is selected from the group consisting of stylets, spiral wires, braids, stiffening wires, stiffening rings, stiffening coatings, stiffening meshes, and removably insertable stiffening elements.

8. The device of claim 1, wherein the elongate shaft comprises a catheter and the treatment member comprises an inflatable member.

9. The device of claim 8, wherein the shaft further comprises an inflation lumen in communication with the inflatable member.

10. The device of claim 9, wherein the shaft further comprises a guidewire lumen for receiving a guidewire.

11. The device of claim 1, wherein the elongate shaft defines at least one lumen.

12. The device of claim 11, further comprising a malleable member insertable into the at least one lumen, wherein the malleable member is configured to impart malleability to the elongate shaft when the malleable member is inserted into the at least one lumen.

13. The device of claim 11, further comprising an insertable element, wherein the insertable element has a pre-formed shape, wherein the shaft is configured to assume the pre-formed shape of the insertable element when the insertable element is inserted into the at least one lumen.

14. The device of claim 1, further comprising a tensile element coupled to the distal end portion of the shaft, wherein the shaft is configured to bend in response to the tensile element being pulled in the proximal direction.

15. The device of claim 1, wherein the tip is configured to return to the first position when the second portion of the deflecting member is moved distally.

16. The device of claim 1, further comprising at least one shaft stiffening member coupled with the elongate shaft for stiffening the flexible portion;
   wherein the shaft stiffening member is configured to transition between a first position and second position;
   wherein the flexible portion of the elongate shaft is flexible when the at least one shaft stiffening member is in the first position;
   wherein the flexible portion of the elongate shaft is stiff when the at least one shaft stiffening member is in the second position; and
   wherein the tip is configured to be deflected when the flexible portion of the elongate shaft is flexible.

17. A device for treating a patient, the device comprising:
   (a) a treatment member;
   (b) a shaft coupled with the treatment member, wherein the shaft comprises:
      (i) a proximal end,
      (ii) a distal end,
      (iii) an exterior surface,
      (iv) a tip disposed on the distal end and having an outer diameter sized to allow the shaft to be inserted into a patient's nose, and
      (v) a flexible portion coincident with the treatment member and coupled with the tip, wherein the flexible portion is configured to deflect the tip between a first position and a second position;
   (c) a handle extending from the shaft;
   (d) a steering wire coaxial with the treatment member, wherein the steering wire is movable between a first steering position and a second steering position; and
   (e) a slide element, wherein the slide element is slidably coupled with the handle and the steering wire, wherein the slide element is movable between a first slide position and a second slide position, wherein the slide element is operable to move the steering wire to the first steering position in response to movement of the slide element to the first slide position, wherein the slide element is operable to move the steering wire to the second steering position in response to movement of the slide element to the second slide position.

18. A device for treating a patient, the device comprising:
(a) an elongate, at least partially flexible shaft comprising:
   (i) a proximal end,
   (ii) a distal end,
   (iii) a tip at or near the distal end, and
   (iv) a flexible portion at or near the distal end, wherein at least a portion of the shaft extends along an axis;
(b) a treatment member coupled with the shaft, wherein the flexible portion of the shaft is coincident with the treatment member such that at least a portion of the tip is deflectable between a first angle relative to the axis and a second angle relative to the axis;
(c) a steering wire coincident with the treatment member and configured to be selectively advanced and retracted therethrough; and
(e) a thumb slide, wherein the thumb slide is coupled with the steering wire and movable along a track.

19. The device of claim 18, wherein the thumb slide is operable to advance the steering wire in response to movement of the thumb slide in a first direction.

20. The device of claim 19, wherein the thumb slide is operable to retract the steering wire in response to movement of the thumb slide to a second direction.

\* \* \* \* \*